US005714374A

United States Patent [19]
Arnold et al.

[11] Patent Number: 5,714,374
[45] Date of Patent: *Feb. 3, 1998

[54] CHIMERIC RHINOVIRUSES

[75] Inventors: Edward V. Arnold; Gail Ferstandig Arnold, both of New Brunswick, N.J.

[73] Assignee: Rutgers University, Piscataway, N.J.

[ * ] Notice: The term of this patent shall not extend beyond the expiration date of Pat. No. 5,541,100.

[21] Appl. No.: 406,347

[22] Filed: Mar. 17, 1995

Related U.S. Application Data

[63] Continuation-in-part of Ser. No. 304,635, Sep. 12, 1994, Pat. No. 5,541,100, which is a continuation of Ser. No. 41,790, Apr. 1, 1993, abandoned, which is a continuation of Ser. No. 582,335, Sep. 12, 1990, abandoned.

[51] Int. Cl.[6] .............................. C12N 7/01; A67K 39/12

[52] U.S. Cl. .................. 435/235.1; 424/93.6; 435/172.3
[58] Field of Search .............................. 435/235.1, 172.3; 424/93.2, 93.6, 199.1

[56] References Cited

U.S. PATENT DOCUMENTS 5,541,100 7/1996 Arnold et al. ........................ 435/235.1

OTHER PUBLICATIONS

Abraham and Colonno, "Many Rhinovirus Serotypes Share the Same Cellular Receptor", *J. Virol.*, vol. 51 pp. 340–345, 1984.

Ada & Skehel, "Are peptides good antigens?" *Nature*, vol. 316, pp. 764–765, 1985.

Ahlers, J. D., et al., "Construction of an HIV–1 peptide vaccine containing a multideterminants helper peptide linked to a V3 loop peptide 18 inducing strong neutralizing antibody responses in mice of multiple MHC haplotypes after two immunizations," *J. Immunol.*, vol. 150 pp. 5647–5665, 1993.

Anderson, K.P. et al., "Effect of dose and immunization schedule on immune response of baboons to recombinant glycoprotein 120 of HIV–1," *J. Infect. Dis.*, vol. 160, pp. 960–969, 1989.

Arnold et al., "The Use of Molecular–Replacement Phases for the Refinement of the Human Rhinovirus 14 Structure," *J. Mol. Biol.*, vol. 210 pp. 91–111, 1989.

Arnold et al., "The Use of Molecular–Replacement Phases for the Refinement of the Human Rhinovirus 14 Structure", *Acta Cryst.*, vol. A44 pp. 270–282, 1988.

Arnold et al., "Analysis of the Structure of a Common Cold Virus, Human Rhinovirus 14, Refined at a Resolution of 3.0A," *J. Mol. Biol.*, vol. 211 pp. 763–801, 1990.

Barrett, N. et al., "Large–scale production and purification of a vaccinia recombinant–derived HIV–1 gp160 and analysis of its immunogenicity," *AIDS Res. Hum. Retroviruses*, vol. 5, pp. 159–171, 1989.

Belo, M. et al., "Antibody–dependent cellular cytotoxicity against HIV–1 in sera of immunized chimpanzees," *AIDS*, vol. 5, pp. 169–176, 1991.

Belshe, R. B. et al., "Safety and immunogenicity of a fully glycosylated recombinant gp160 human immunodeficiency virus type 1 vaccine in subjects at low risk of infection." *J. Infec. Dis.*, vol. 168, pp. 1387–1395, 1993.

Berman, P. W., et al., "Expression and immunogenicity of the extracellular domain of the human immunodeficiency virus type 1 envelope glycoprotein, gp160," *J. Virol.*, vol. 63, pp. 3489–3498, 1989.

Berman, P. W. et al., "Neutralization of multiple clinical isolates of HIV–1 by antisera raised against a monovalent subunit vaccine," *Sixieme Colloque des Cent Gardes*, pp. 293–297, 1991.

Berman, P. W. et al., "Protection of chimpanzees from infection by HIV–1 after vaccination with recombinant glycoprotein gp120 but not gp160," *Nature*, vol. 345, pp. 622–625, 1990.

Bittle, et al., "Protection against foot–and–mouth disease by immunization with a chemically synthesized peptide predicted from the viral nucleotide sequence," *Nature*, vol. 298, pp. 30–33, 1982.

Burke, et al., "A Cassette Vector for the Construction of Antigen Chimaeras of Poliovirus," *J. Gen. Virol.*, vol. 70 pp. 2475–2479, 1989.

Callahan, et al., "Molecular cloning and complete sequence determination of RNA genome of human rhinovirus type 14," *Proc. Natl. Acad. Sci. U.S.*, vol. 82 pp. 732–736, 1985.

Conant and Hamparian, "Rhinoviruses: Basis for a Numbering System," *J. Immunol.*, vol. 100, pp. 107–113, 1968.

Cooney, E. L. et al., "Enhanced immunity to human immunodeficiency virus (HIV) envelope elicited by a combined vaccine regimen consisting of priming with a vaccinia recombinant expressing HIV envelope and boosting with gp160 protein," *Proc. Natl. Acad. Sci. USA*, vol. 90, pp. 1882–1886, 1993.

Dedieu, J.F. et al., "Poliovirus chimeras expressing sequences from the principal neutralization domain of human immunodeficiency virus type 1," *J. Virol.*, vol. 66, pp. 3161–3167, 1992.

Defoort, J. P., et al., "Macromolecular assemblage in the design of a synthetic AIDS vaccine," *Pro. Natl. Acad. Sci. USA*, vol. 89, pp. 3879–3883, 1992.

Delpeyroux, et al., "A Poliovirus Neutralization Epitope Expressed on Hybrid Hepatitis B Surface Antigen Particles," *Science*, vol. 233, pp. 472–475, 1986.

DiMarchi, et al., "Protection of Cattle Against Foot–and–Mouth Disease by a Synthetic Peptide," *Science*, vol. 232 pp. 639–641, 1986.

Dolin, R. et al., "The safety and immunogenicity of a human immunodeficiency virus type (HIV–1) recombinant gp160 candidate vaccine in humans," *Ann. Intern. Med.*, vol. 114, pp. 119–127, 1991.

Englund, G., et al., "A Novel HIV–1 Isolate Containing Alterations Affecting the NF–$_{\kappa}$B Element," *Virology*, vol. 181 pp. 150–157, 1991.

Evans, DJ, et al., "An engineered poliovirus Chimaera elicits broadly reactive HIV–1 neutralizing antibodies," *Nature*, vol. 1339 pp. 3851–3881, 1989.

Frommhagen, "The Separation and Physicochemical Properties of the C and D Antigens of Coxsackievirus," *J. Immunol.*, vol. 95, pp. 818–822, 1965.

Fultz, P. N. et al., "Vaccine protection of chimpanzees against challenge with HIV–1 infected peripheral blood mononuclear cells." *Science*, vol. 256, pp. 1687–1690, 1992.

Gallo, R.C., et al., "Frequent Detection and Isolation of Cytopathic Retroviruses (HTLV–III)from Patients with AIDS and at Risk for AIDS," *Science*, vol. 224 pp. 500–503, 1984.

Ghiara, J., B., et al., "Crystal Structure of the Principal Neutralization Site of HIV–1," *Science*, vol. 264 pp. 82–85, 1994.

Girard, M. et al., "Immunization of chimpanzees confers protection against challenge with human immunodeficiency virus." *Proc.Natl. Acad. Sci. USA*, vol. 88 pp. 542–546, 1991.

Gorny, M. K., et al., "Neutralization of Diverse Human Immunodeficiency Virus Type 1 Variants by an Anti–V3 Human Monoclonal Antibody," *J. Virol.*, vol. 66 pp. 7538–7542, 1992.

Gorse, G. J. et al., "HIV–1 recombinant gp160 vaccine given in accelerated dose schedules," *Clin. Exp. Immunol.*, vol. 98, pp. 178–184, 1994.

Gorse, G. J. et al., "Evaluation of HIV–1 MN V3 octameric peptide vaccine," *Seventh Annual Meeting of the National Cooperative Vaccine Development Groups for AIDS*, p. 94, 1994.

Goudsmit, J., et al., "Human immunodeficiency virus type 1 neutralization epitope with conserved architecture elicits early type–specific antibodies in experimentally infected chimpanzees," *Proc. Natl. Acad. Sci. USA*, vol. 85 pp. 4478–4482, 1988.

Graham, B. S. et al., "Augmentation of human immunodeficiency virus type 1 neutralizing antibody by priming with gp160 recombinant vaccinia and boosting with rgp160 in vaccinia–naive adults," *J. Infect. Dis.*, vol. 167, pp. 533–537, 1993.

Griffiths, J.C., et al., "Induction of high–titer neutralizing antibodies using hybrid human immunodeficiencyvirus V3–Ty virus like particles in a clinically relevant adjuvant.," *J. Virol.*, vol. 65, pp. 450–456, 1991.

Haffar, O.K., et al., "HIV–specific humoral and cellular immunity in rabbits vaccinated with recombinant human immunodeficiency virus–like gag–env particles.," *Virology*, vol. 183, pp. 487–495, 1991.

Kahn, J. O., et al., "Clinical and immunologic responses to human immunodeficiency virus (HIV) type 1 $_{sf2}$ gp120 subunit vaccine combined with MF59 adjuvant with or without muramyl tripeptide dipalmitoyl phosphatidylethanolamine in non–HIV–infected human volunteers," *J. Infect. Dis.*, vol. 170, pp. 1288–1291, 1994.

Kahn, J. O., et al., "A phase I study of HGP–30, a 30 amino acid subunit of the human immunodeficiency virus (HIV) p17 synthetic peptide analogue subunit vaccine in seronegative subjects," *AIDS Res. Hum. Retroviruses*, vol. 8, pp. 1321–1325, 1992.

Keller, P. M. et al., "Identification of HIV vaccine candidate peptides by screening random phage epitope libraries," *Virology*, vol. 193, pp. 709–716, 1993.

Kohara, M. et al., "A Recombinant Virus between the Sabin 1 and Sabin 3 Vaccine Strains of Poliovirus as a Possible Candidate for a New Type 3 Poliovirus Live Vaccine Strain," *J. Virol.*,vol. 62, pp. 2828–2835, Aug. 1988.

Kovacs, J.A. et al., "Induction of humoral and cell–mediated anti–human immunodeficiency virus (HIV) responses in HIV sero–negative volunteers by immunization with recombinant gp160," *J. Clin. Invest.*, vol. 92 pp. 919–298, 1993.

Kunkel et al., "Rapid and Efficient Site-Specific Mutagenesis without Phenotypic Selection," *Meth. Enzymol.*, vol. 154, pp. 367–382, 1987.

Kunkel, et al., "Rapid and efficient site–specific mutagenesis without phenotypic selection," *Proc. Natl. Acad. Sci., U.S.A.*, vol. 82, pp. 488–492, 1985.

LaRosa, G. J., et al., "Conserved Sequence and Structural Elements in the HIV–1 Principal Neutralizing Determinant," *Science*, vol. 249, pp. 932–935, 1990.

Lee, W.M. et al., "Role of Maturation Cleavage in Infectivity of Picornaviruses: Activation of an Infectosome," *J. Virol.*, vol. 67, pp. 2110–2112, 1993.

Leszczynski et al., "Loops in Globular Proteins: A Novel Category of Secondary Structure," *Science*, vol. 234, pp. 849–855, 1986.

Li, S. et al., "Chimeric influenza virus induces neutralizing antibodies and cytotoxic T cells against human immunodeficiency virus type 1," *J. Virol.*, vol. 67, pp. 6659–6666, 1993.

Lonberg–Holm et al., "Antigenic Determinants of Infective and Inactivated Human Rhinovirus Type 2," *J. Virol.*, vol. 12 pp. 114–123, 1973.

Mann, D.L., et al., "Origin of the HIV–Susceptible Human CD4+ Cell Line H9," *AIDS Res. Hum. Retroviruses*, vol. 5 pp. 253–255, 1989.

Martin, et al., "Engineering a poliovirus type 2 antigenic site on a type 1 capsid results in a chimaeric virus which is neurovirulent for mice," *EMBO J.*,vol. 7 pp. 2839–2847, 1988.
Masuda, T., et al., "Generation of Neutralization–Resistant HIV–1 in Vitro Due to Amino Acid Interchanges of Third Hypervariable Env Region," *J. Immunol.*, vol. 145, pp. 3240–3246, 1990.
Matsushita, S., et al., "Characterization of a Human Immunodeficiency Virus Neutralizing Monoclonal Antibody and Mapping of the Neutralizing Epitope," *J. Virol.*, vol. 62, pp. 2107–2114, 1988.
Mayer, et al., "The purification of Poliomyelitis Virus as Studied by Complement Fixation," *J. Immunol.*, vol. 78, pp. 435–455, 1957.
Mizutani, S., et al., "In Vitro Synthesis of an Infectious RNA from cDNA Clones of Human Rhinovirus Type 14," *J. Virol.*, vol. 56, pp. 628–632, Nov. 1985.
Muster, T. et al., "Cross–neutralizing activity against divergent human immunodeficiency virus type 1 isolates induced by the gp41 sequence ELDKWAS," *J. Virol.*, vol. 68, pp. 4031–4034, Jun. 1994.
Natuk, R. J., et al., "Adenovirus–human immunodeficiency virus (HIV) envelope recombinant vaccines elicit high–titered HIV–neutralizing antibodies in the dog model," *Proc. Natl. Acad. Sci. USA*, vol. 89, pp. 7777–7781, 1992.
Natuk, R. J., et al., "Immunogenicity of recombinant human adenovirus–human immunodeficiency virus vaccines in chimpanzees," *AIDS Res. Hum. Retroviruses*, vol. 9, pp. 395–404, 1993.
Ohno, T., et al., "A broadly neutralizing monoclonal antibody that recognizes the $V_3$ region of human immunodeficiency virus type 1 glycoprotein gp120," *Proc. Natl. Acad. Sci. USA*, vol. 88, pp. 10726–10729, 1991.
Panicali, D. et al., "Construction of live vaccines by using genetically engineered poxviruses: Biological activity of recombinant vaccinia virus expressing influenza virus hemagglutinin", *Proc. Nat. Acad. Sci.*, vol. 80 pp.5364–5368, Sep. 1983.
Pfaff, et al., "Antibodies against a preselected peptide recognize and neutralize foot and mouth disease virus," *EMBO. J.*, vol. 1, pp. 869–874, 1982.

Picard, O. et al., "A 2-year follow-up of an anti-HIV immune reaction in HIV-1 gp160-immunized healthy seronegative humans: evidence for persistent cell-mediated immunity," *J. Acquir. Immune Defic. Syndr.*, vol. 5, pp. 539–546, 1992.

Powell, M. F., et al., "Immunogenicity and HIV-1 virus neutralization of MN recombinant glycoprotein 120/HIV-1 QS21 vaccine in baboons," *AIDS Res. Hum. Retroviruses*, vol. 10, pp. S105–S108, 1994.

Resnick, D.A., et al., "Chimeras from a human rhinovirus 14: human immunodeficiency virus Type 1 V3 loop seroprevalence library induce neutralizing responses against HIV-1", *J. Virology*, Apr. 1995 pp. 2406–2411.

Rico-Hesse, et al., "Geographic Distribution of Wild Poliovirus Type 1 Genotypes," *Virology*, vol. 160, pp. 311–322, 1987.

Rini, J. M., et al., "Crystal structure of a human immunodeficiency virus type 1 neutralizing antibody, 50.1, in complex with its V3 loop peptide antigen," *Proc. Natl. Acad. Sci. USA*, vol. 90, pp. 6325–6329, 1993.

Rossman, et al., "Structure of a human common cold virus and functional relationship to other picornaviruses," *Nature*, vol. 317, pp. 145–153, 1985.

Rowlands, et al., "A Comparative Chemical and Serological Study of the Full and Empty Particles of Foot-and-Mouth Disease Virus," *J. Gen. Virol.*, vol. 26, pp. 227–238, 1975.

Rusche, et al., *Proc. Natl. Acad. Sci.*, USA, 85:3198–3202, 1988.

Sanger, et al., "DNA Sequencing with chain-terminating inhibitors," *Proc. Natl. Acad. Sci. U.S.A.*, vol. 74, pp. 5463–5467, 1977.

Schlienger, K. et al., "Human immunodeficiency virus type 1 major neutralizing determinant exposed on hepatitis B surface antigen particles is highly immunogenic in primates," *J. Virol.*, vol. 65, pp. 450–456, 1992.

Schwarts, David H., et al., "Induction of HIV-1-neutralizing and syncytium-inhibiting antibodies in uninfected recipients in HIV-1 rgp120 subunit vaccine," *The Lancet*, vol. 342 pp. 69–73, Jul. 10, 1993.

Serghini, et al., "A rapid and efficient 'miniprep' for isolation of plasmid DNA," *Nucleic Acids Res.*, vol. 17 p. 3604, 1989.

Shaw, G. M. et al., "Molecular Characterization of Human T-Cell Leukemia (Lymphotropic) virus Type III in the Acquired Immune Deficiency Syndrome," *Science*, vol. 226 pp. 1165–1171, 1984.

Sherry et al., "Evidence for at Least Two Dominant Neutralization Antigens on Human Rhinovirus 14," *J. Virol.* vol. 53, pp. 137–143, 1985.

Sherry, et al., "Use of Monoclonal Antibodies to Identify Four Neutralization Immunogens on a Common Cold Picornavirus, Human Rhinovirus 14," *J. Virol.*, vol. 57, pp. 246–257, 1986.

Smith, A.D., et al., "Use of Random Systematic Mutagenesis To Generate Viable Human Rhinovirus 14 Chimeras Displaying Human Immuondeficiency Virus Type 1 V3 Loop Sequences," *J. Virol.*, vol. 68, pp. 575–579, 1994.

Stanway, et al., "The complete nucleotide sequence of a common cold virus: human rhinovirus 14," *Nucl. Acids Res.*, vol. 12, pp. 7859–7875, 1984.

Steimer, K.S. et al., "Recombinant env and gag polypeptides in characterizing HIV-1-neutralizing antibodies," *Vaccines*, vol. 88, pp. 347–355, 1988.

Tiollais, et al., "The hepatitis B virus," *Nature*, vol. 317, pp. 489–495, 1985.

Tolman, R. L., et al., "Cyclic V3-loop-related HIV-1 conjugate vaccines," *Int. J. Pept. Pro. Res.*, vol. 41, pp. 455–466, 1993.

Urakawa, et al., "Synthesis of Immunogenic, but Non-infectious, Poliovirus Particles in Insect Cells by a Baculovirus Expression Vector," *J. Gen. Virol.*, vol. 70, pp. 1453–1463, 1989.

Wang, J. J. G., et al., "Detection of antibodies to human T-lymphotropic virus type III by using a synthetic peptide of 21 amino acid residues corresponding to a highly antigenic segment of gp41 envelope protein," *Proc. Natl. Acad. Sci. USA*, vol. 83, pp. 6159–6163, 1986.

Wang, C. Yu., et al., "Long-term high-titer neutralizing activity induced by octameric synthetic HIV-1 antigen," *Science*, vol. 254, pp. 285–288, 1991.

Wang, B. et al., "Gene inoculation generates immune response against human immunodeficiency virus type 1," *Proc. Natl. Acad. Sci. USA*, vol. 90, pp. 4156–4160, 1993.

White-Scharf, M. E., et al., "Broadly Neutralizing Monoclonal Antibodies to the V3 Region of HIV-1 Can Be Elicited by peptide Immunization," *Virology*, vol. 192, pp. 197–206, 1993.

Wiegers et al., "Monospecific Antisera Against Capsid Polypeptides of Poliovirus Type 1 Distinguish Antigenic Structures of Poliovirus Proteins," *J.Gen. Virol.*, vol. 64, pp. 777–785, 1983.

Willey, R. L., et al., "In Vitro Mutagenesis Identifies a Region within the Envelope Gene of the Human Immunodeficiency Virus That Is Critical for Infectivity," *J. Virol.*, vol. 62, pp. 139–147, 1988.

Yanish-Perron, Celeste et al., "Improved M3 phage cloning vectors and host strains: nucleotide sequences of the M13mp18 and pUC19 vectors," *Gene*, vol. 33, 1985, pp. 108–119.

Zagury, D. et al., "A group specific anamnestic immune reaction against HIV-1 induced by a candidate vaccine against AIDS," *Nature*, vol. 332, pp. 728–731, 1988.

Zhang, A., et al., "Structure Determination of Antiviral Compound SCH 38057 Complexed with Human Rhinovirus 14," *J. Mol. Biol.*, vol. 230, pp. 857–867, 1993.

Palker, Thomas J., et al., *Type-Specific Neutralization of the Human Immunodeficiency Virus* . . . , Proc. Natl. Acad. Sci. USA, Mar. 1988, 85:1932–1936.

Andries, Koen, et al., *Two Groups of Rhinoviruses Revealed by a Panel of Antiviral Compounds* . . . , J. of Virol., Mar. 1990, 64:1117–1123.

Appleyard, G., et al., *Neutralization Epitopes of Human Rhinovirus Type 2*, J. of Gen Virol., 1990, 71:1275–1281.

Barnett, et al., *Monoclonal Antibodies to a Peptide of Human Rhinovirus Type 2* . . . , J. of Gen Virol., 1995, 76:1255–1261.

Duechler, M., et al., *Human Rhinovirus Serotype 2: In Vitro Synthesis of an Infectious RNA*, Virology, 1989, 168:159–161.

Gwaltney, Jr., Jack M., Rhinoviruses, in *Viral Infection of Humans, Epidemology and Contol*, Evans, A.S. (ed), 1989, New York, Plenum Medical, 3rd Edition, pp. 593–615.

Horsnell, C., et al., *Molecular Relationships Between 21 Human Rhinovirus Serotypes*, J. of Gen. Virol., 1995, 76:2549–2555.

Kandolf, R., et al., *Molecular Cloning of the Genome of a Cardiotropic Coxsackie B3 Virus* . . . , Proc. Natl. Acad. Sci. USA, Jul. 1985, 82:4818–4822.

Kim, S., et al., *Crystal Structure of Human Rhinovirus Serotype 1A(HRV1A)*, J. Mol. Biol., 1989, 210:91–111.

Kohara, M., et al., *An Infectious cDNA Clone of the Poliovirus Sabin Strain Could Be Used* . . . , Virology, 1986, 151:21–30.

Lee, Wai–Ming, et al., *Role of Maturation Cleavage in Infectivity of Picornaviruses* . . . , J. of Virol., Apr. 1993, 67:2110–2122.

Mizutani, S., et al., *In Vitro Synthesis of an Infectious RNA from cDNA Clones* . . . , J. of Virol., Nov. 1995, 56:628–632.

Oliveira, M.A., et al., *The Structure of Human Rhinovirus 16*, Structure, Sep. 1993, 1:51–68.

Omata, T., et al., *Cloned Infesctious Complementary DNA of the Poliovirus Sabin 1 Genome:* . . . , Gene, 1984, 32:1–10.

Palmenberg, A.C., *Sequence Alignments of Picornaviral Capsid Proteins*, Molecular Aspects of Picornavirus Infection and Detection, Bert L. Semler, et al., eds., 1989, Chapter 13, pp. 211–241.

Racaniello, V.R., et al., *Cloned Poliovirus Complementary DNA Is Infectious in Mammalian Cells*, Science, 20 Nov. 1981, 214:916–919.

Resnick, D.A. et al., *Chimeras from a Human Rhinovirus 14–Human Immunodeficiency Virus* . . . , J. of Virol., Apr. 1995, 69:2406–2411.

Rossmann, M.G., et al., *Structure of a Human Common Cold Virus and* . . . , Nature, Sep. 1985, 317:145–153.

Semler, B., et al., *Production of Infectious Poliovirus from Cloned cDNA is Dramatically Increased* . . . , Nucleic Acids Research, 1984, vol. 12, No. 12.

Sherry, B., et al., *Use of Monoclonal Antibodies to Identify Four Neutralization Immunogens* . . . , J. of Virol., Jan. 1986, 57:246–267.

Smith, A.D., et al.,1 *Use of Random Systematic Mutagenesis to Generate Viable Human Rhinovirus* . . . , J. of Virol., Jan. 1994, 68:575–579.

Speller, S.A., et al., *The Nature and Spatial Distribution of Amino Acid Substitutions* . . . , J. of Gen. Virol., 1993, 74:193–200.

Uncapher, C.R., et al., *The Major and Minor Group Receptor Families Contain All but One Human Rhinovirus Serotype*, Virology, 1991, 180:814–817.

*Primary Examiner*—Nancy Degen
*Attorney, Agent, or Firm*—Kenyon & Kenyon

[57] ABSTRACT

Various novel recombinant chimeric human rhinoviruses are disclosed, including viruses comprising human rhinovirus 14 into which chimeric regions derived from influenza HA, poliovirus and HIV-1 have been incorporated. Chimeric human rhinoviruses are particularly advantageous as they are only mildly pathogenic, have numerous potential serotypes and can elicit significant mucosal and serum immunological response. Design considerations, methods, and examples are described. The chimeric rhinoviruses can be used as vaccines and for a variety of other immunotechnological applications including passive immunization, immunodiagnostic testing and antigenicity and immunogenicity studies.

27 Claims, 1 Drawing Sheet

CHIMERIC RHINOVIRUSES

This application is a Continuation-in-part of U.S. Ser. No. 08/304,635 filed Sep. 12, 1994, now U.S. Pat. No. 5,541,100, which is a continuation of Ser. No. 08/041,790, filed Apr. 1, 1993, now abandoned, which in turn is a continuation of Ser. No. 07/582,335, filed Sep. 12, 1990, now abandoned.

The U.S. Government has a paid-up license in this invention and the right in limited circumstances to require the patent owner to license others on reasonable rems, as provided for by the terms of NIH National Cooperative Vaccine Grant AI30238.

FIELD OF THE INVENTION

The invention relates to recombinant chimeric human viruses that contain genetic material derived from other viruses. More particularly, the present invention relates to human rhinoviruses that contain a chimeric portion derived from other viruses. These rhinovirus chimeras can be used to stimulate an immune response, and thus can serve as vaccines, or to stimulate antibody production for use, for example, in immunodiagnostic systems or for passive immune purposes. They can also be used as antigens in methods used to detect the presence of antibodies.

DESCRIPTION OF THE BACKGROUND ART

The production of effective and safe vaccines against harmful viruses and other pathogens continues to be a difficult endeavor. To date, the most successful vaccines involve the use of inactivated viruses or live attenuated viruses obtained from multiple passages of wild-type viruses in tissue culture or in non-human primates. A concern that still lingers, however, is that outbreaks occasionally occur, apparently from improper inactivation of the viruses, reversion or pseudoreversion of the viruses to virulent strains, extension of the host range, and/or contamination of vaccines with live virus.

To overcome some of these complications, considerable research effort has been expended to examine the feasibility and efficacy of immunizing with empty viral capsids and pathogen-derived proteins and peptides. Unfortunately, the antigenicity profiles for complex virions and empty capsids are often quite different. This phenomenon has been documented for several picornaviruses, including rhinovirus (Lonberg-Holm & Yin, J. Virol., 12:114–123, 1973), poliovirus (Mayer, et al., J. Immunol., 78:435–455, 1957), foot-and-mouth disease virus (FMDV) (Rowlands, et al., J. Gen. Virol., 26:227–238, 1975), and Coxsackie B virus (Frommhagen, J. Immunol., 95:818–822, 1965). Studies with individual virion proteins have shortcomings as well. Individual coat proteins, for instance, have antigenic determinants absent from intact viruses (Wiegers & Derrick, J. Gen. Virol., 64:777–785, 1983) and are generally far less effective at stimulating neutralizing antibodies than are whole virions. Attempts to use peptides to provide protection against dangerous pathogens have also been disappointing. Despite occasional examples of success (e.g., Bittle, et al., Nature, 298:30–33, 1982; Pfaff, et al., EMBO. J., 1:869–874, 1982), most peptides fail to protect vaccinated animals, even when they are capable of stimulating the production of neutralizing antibodies (e.g., Ada & Skehel, Nature, 316:764–765,1985; Tiollais, et al., Nature, 317:489–495, 1985; DiMarchi, et al., Science, 232:639–641, 1986).

A more recent approach to vaccine development and the one which is utilized in the present invention uses chimeric viruses or virus-like particles (VLPs) as vehicles for presentation of foreign antigens to the immune system. A number of virus-like panicles (VLPs) composed of fusion proteins have been shown to test positively in standard enzyme-linked immunosorbent assays (ELISAs) with antibodies directed against either substituent of the fusion protein. Among chimeric VLPs, almost none have been tested for their ability to protect infected animals; an exceptional case involved the testing of a hepatitis B surface antigen:poliovirus VPI chimera which, when injected into mice, produced only weak protection against poliovirus (Delpeyroux, et al., Science, 233:472–475,1986). Live recombinant viruses with the composite antigenicity of mixed poliovirus types have recently been produced in other laboratories (Kohara, et al., J. Virol., 62:2828–2835, 1988; Martin, et al., EMBO. J., 7:2839–2847, 1988; Burke, et al., J. Gen. Virol., 70:2475–2479, 1989); these reports gave no reference to testing of these live chimeras for protection against the virus. In another experiment, Evans, et al., (Nature, 339:385–388, (1989)) incorporated an epitope (positions 735–752) from the transmembrane glycoprotein of HIV-1, gp41, into the neutralizing antigenic region of VPI (N-Ag1) of poliovirus 1 Sabin. These workers reported that rabbit antisera and monoclonal antibodies elicited by the chimera were capable of neutralizing in vitro a wide range of American and African isolates of HIV-1. Protection studies were not reported with this construct.

Unfortunately, previously developed chimeric viruses, such as those based on poliovirus and vaccinia virus, have certain characteristics which make them less than ideal. One of the most significant drawbacks to these chimeric viruses is that their effectiveness as vaccines is limited since many individuals already have a significant immune response to the native virus. Also, at least in the case of poliovirus, the use of a live vaccine carries with it the fact that the native virus is a major pathogen with associated risks.

A cDNA clone of HRV14 was reported by Mizutani and Colonno (J. Virol., 56:628, 1985). This clone of HRV14 purportedly has been utilized to make single-site mutations in the coat proteins primarily for the purpose of examining the properties of the cell receptor attachment site on the viral surface (Colonno, et al. 1988). However, successful construction of immunogenic chimeras of HRV14, or any other HRV, has not been reported.

An improved way to stimulate an immune response using a chimeric virus would be to utilize a native virus which, (1) is a relatively mild pathogen, such that little risk would be associated with the use of a live chimeric virus vaccine; (2) has a broad range of serotypic diversity (>100 serotypes), lessening the likelihood of preexisting immunity and thereby enabling vaccination in adults; and (3) has the ability to stimulate a significant neutralizing immune response in mucosal membranes as well as in serum. The present invention provides a means for accomplishing this result.

SUMMARY OF THE INVENTION

The present invention arose out of the discovery that a recombinant chimeric human rhinovirus could be produced which, when introduced into a host, stimulates an immune response in the host to the chimeric portion of the recombinant rhinovirus. The chimeric portions, or regions, are exposed as part of viral surface proteins such that their presence does not prevent the reproduction of the viable virus. The chimeric portion is incorporated into the virus by inserting a nucleotide fragment with a base sequence encoding the chimeric portion into a plasmid used to generate the viral genome, such that the inserted nucleotide changes will be expressed as part of the surface protein of the rhinovirus. The chimeric region is exposed and accessible to the immune system of a host being immunized with the chimeric rhinovirus.

The present invention comprises at its most fundamental level recombinantly modified chimeric human rhinoviruses. Such chimeric human rhinoviruses meet the criteria noted above; they are (1) relatively mild pathogens, rendering them relatively risk free to those who undergo either intentional exposure (such as those who are being vaccinated) or to those who undergo accidental exposure (such as researchers in the field of immunology and health care providers); (2) have a broad range of serotypic diversity, improving the ability to avoid preexisting immunities and (3) can produce robust and long-lasting mucosal and serum-mediated immunity. These rhinoviruses can be used to vaccinate a human or other animal such that an immune response is produced to the chimeric portion of the rhinovirus. The chimeric rhinovirus can also be used, along with various antibody preparations, to generate antigenicity profiles. These profiles can be used, for example, as a tool to predict antigenicity (an ability to react with pre-existing antibodies) and immunogenicity (an ability to elicit production of antibodies). Moreover, the three dimensional structure of the various chimeric rhinoviruses can be determined and compared to study the structural determinants of immunogenicity. Such epitope characterization will yield detailed information on the structure of various epitopes, even those that are discontinuous; such information will allow for the optimization of chimeras for vaccine use. The chimeric rhinoviruses also can be used for a variety of other immunotechnological applications, such as stimulating the production of antibodies in animals. Such antibodies can then be used, for example, in immunodiagnostic tests or for passive immunization against disease. Alternatively, the chimeric rhinoviruses themselves can be used as antigens, for example, in immunodiagnostic tests to determine if patients have antibodies to a particular pathogen in their blood, which would indicate present or past infection or exposure.

More particularly, the modified chimeric human rhinoviruses of the present invention can be used to characterize in atomic detail the sequence and structural elements that define, for example, immunogenic sequences of the human immunodeficiency virus, HIV-1, which causes Acquired Immune Deficiency Syndrome (AIDS). Many laboratories have experienced tremendous difficulty obtaining structures of the immunogenic proteins of HIV-1 and other viruses. As an alternative approach, the present invention provides the means for generating chimeric human rhinoviruses (HRVs) that display epitopes of HIV-1 and other viruses in ways that are both antigenic and immunogenic. The present invention can be used to generate libraries of chimeric viruses that differ in their immunological profiles, in order to identify specific features that correlate with immunogenicity, differentiate between antigenicity and immunogenicity, and determine cross-reactivity. Characteristics that account for the strength and breadth of the antigenicity and/or immunogenicity of chimeric viruses selected from these libraries can then be determined.

The chimeric viruses of the present invention can be challenged using different antibody preparations to produce an "antigenicity profile", a quantitative profile of antibody recognition and neutralization. Antigenicity profiles of individual chimeras can be compared using many different antibodies to reveal their immunogenic potential. By studying antigenicity profiles, which can be determined in a matter of days, immunogenicity can be predicted. Then, immunogenicity screening, which can take several months and involve considerable expense, need only be carried out on those chimeras predicted to be immunogenic. Thus, the use of antigenicity profiles can save considerable time and expense that would otherwise be spent doing immunogenicity screening on non-immunogenic chimeras.

Those chimeric viruses that look most promising in terms of both the strength and breadth of their antigenic profiles can be used to immunize animals, such as chimpanzees and guinea pigs. The antisera thus obtained can be tested for their ability to recognize peptides from disparate strains of a specific virus of interest. Antisera can also be tested for their ability to neutralize a virus of interest in cell culture. Based on the results of such tests, the relative utility of the antisera or associated antibodies for diagnostic applications, or the utility of the antibodies for passive immunization of another organism, can be assessed.

Techniques of X-ray crystallography can be used to determine the structures of selected chimeric viruses. This can permit visualization in atomic detail of important virus neutralizing epitopes in immunologically relevant conformations. Such information can be used, for example, to characterize important antigens, and by inference, provide information about their corresponding antibodies, which may be useful for passive immunization or for diagnostic testing. Furthermore, comparisons of the structures of viral epitopes that vary in their strengths and specificities should yield valuable insights into structural determinants of immunogenicity. In addition, such comparisons may help to illuminate such important issues as the differences between antigenicity and immunogenicity, if any, between type-specific and group-specific immune recognition, and between dominant and weak immune responses. The use of the chimeras of the present invention as the object of such an analysis avoids the need to handle live viruses of grave pathogenicity such as HIV, and also allows viral epitopes to be studied separately as well as in various combinations. This will result in a more detailed understanding of the immune recognition of HIV, and should illuminate some of the reasons for failure of some vaccines. This information will also allow for the further optimization of chimeras such as those described here for use in producing antibodies for passive immunization or diagnostic testing, and perhaps more importantly, will allow for the optimization of rhinovirus chimeras and other constructs that can be used as improved vaccines.

DETAILED DESCRIPTION OF THE INVENTION

Figure 1A:
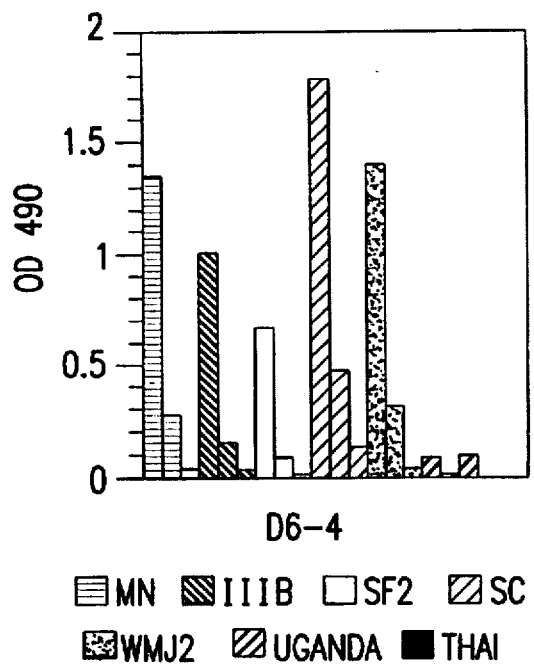
FIGS. 1A–1D show a bar graph representing optical density measurements from ELISA experiments that indicate the reactivity of anti-chimera antisera with V3 loop peptides derived from seven different strains of HIV-1.
Figure 1B:
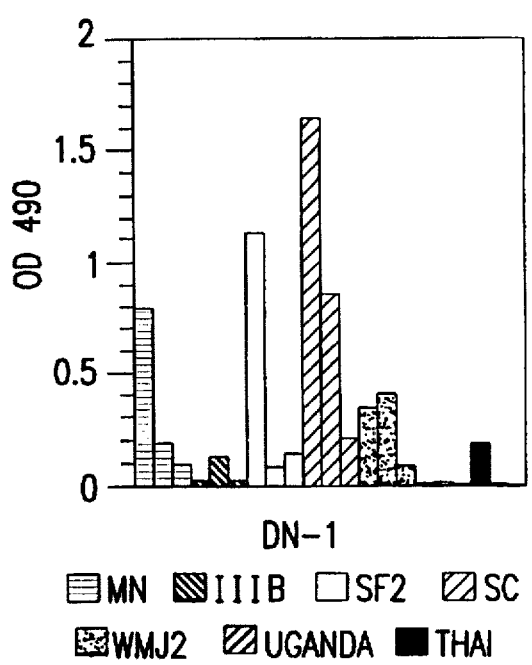
Figure 1C:
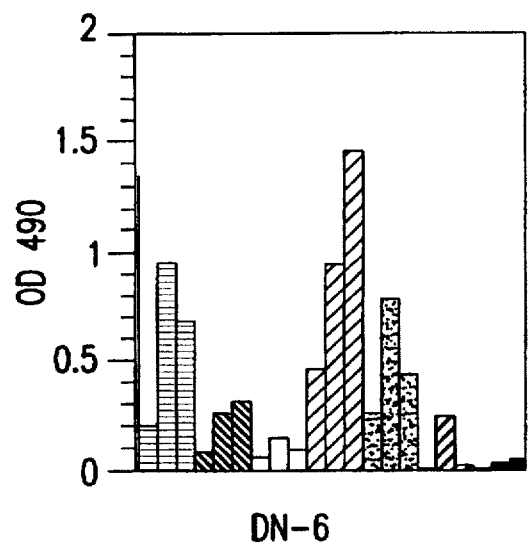
Figure 1D:
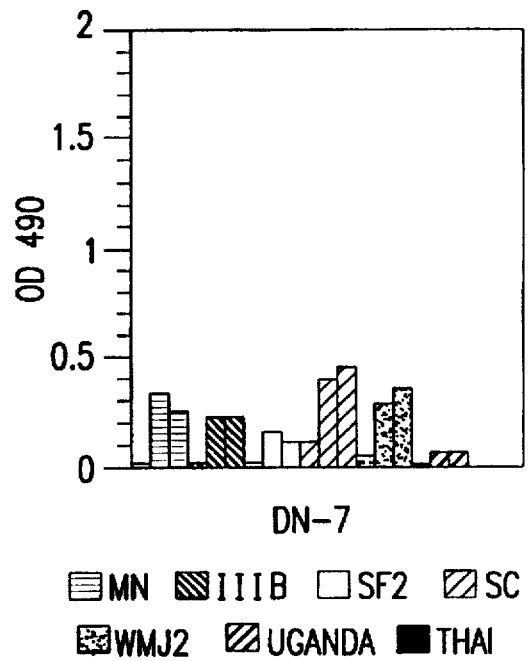

Rhinoviruses are among the major pathogenic agents that cause common colds in humans. There are a number of compelling advantages of using rhinoviruses as live-virus vaccine vectors for human use. Rhinoviruses cause relatively mild and short-term, although annoying, pathogenic symptoms. Rhinoviruses provoke not only a localized mucosal immune response, but also a significant serum immune response. The immune response to rhinovirus infection is long-lasting and can be boosted by reimmunization. Finally, the three-dimensional structure and precise locations of neutralizing immunogenic (NIm) regions of certain rhinoviruses, such as human rhinovirus type 14 (HRV 14), are known, facilitating engineering of foreign epitopes into sites well-recognized by the immune system.

A general misunderstanding persists that HRV infections cause only "superficial" immune responses and HRV-based vaccines would only be relevant and effective for respiratory viral infections. Nasal secretions contain significant neutralizing antibody titers (consisting largely of the IgA subclass) following intranasal (IN) administration of HRVs, and protection against reinfection by homotypic HRV challenge appears to be largely due to the presence of significant IgA neutralizing titers in nasal secretions. In fact, both inactivated HRVs (for example, "killed" by treatment with 0.025% formalin and administered either IN or intramuscularly (IM)) and live HRVs (preferably administered IN) lead to significant neutralizing antibody titers in serum (consisting primarily of IgM and IgG subtypes). While the sensitivities of different tests for measuring neutralizing antibody titers can vary significantly (i.e., by an order of magnitude for poliovirus neutralizing antibody tests (Albrecht, et al., Rev. Infect. Dis., 6:5540–5544, 1984)), a comparison of such titers for HRVs with those for poliovirus (live-attenuated and inactivated poliovirus, both successfully used for vaccination) reveals marked similarity. Indeed, HRVs may stimulate an immune response in a variety of mucosal membranes that could be relevant to a wide variety of diseases.

The production of the chimeric rhinoviruses of the invention can be accomplished using site-directed mutagenesis. This technique involves the hybridization of a mutagenic DNA oligomer encoding the immunogenic chimeric region of choice (employing preferred codon usage for HRV14 wherever possible), with a source of single-stranded template DNA for synthesis of double-stranded plasmid DNA. In cases where single-stranded DNA contains uracil, appropriate bacterial cells can be used to preferentially destroy the uracil-containing strand and replace it with freshly synthesized DNA directed from the mutagenized strand, thus increasing the efficiency of the mutagenesis reaction.

In a particularly preferred embodiment of the invention, it is possible to use site directed mutagenesis to create restriction endonuclease recognition sites that can then be used for cassette mutagenesis, a method described by Smith, A. D., et al., J. Virol. 68: 575–579, 1994. An example of such an approach using the plasmid p3IIST is provided in Example 3 herein below. It is also possible to utilize other techniques such as subcloning, for instance using polymerase chain reaction (PCR) amplification of mutagenic DNA sequences, which are then ligated into pWR40 or other suitable plasmid. In one preferred embodiment, cassette mutagenesis can be done using p3IIST.

It is important to recognize that not all possible chimeric constructs will produce viable chimeric viruses; some insertions appear to interfere with normal viral assembly and/or function. Therefore, it is most advantageous to produce populations of chimeric viruses, rather than producing them one at a time. This can be accomplished, for example, by using randomized linkers, as shown in Example 3.

Mutagenized plasmid DNAs are screened for correctness using restriction digestion analyses, taking advantage of (wherever possible) specific changes in restriction digestion patterns. Labeled nucleic acid probes that are complementary to sequences that have been inserted or removed can also be used to aid in the detection of incorporation of new sequences or loss of old sequences, respectively. Apparently correct DNAs are then used as templates for in vitro transcription reactions, taking advantage of a promoter just upstream of the HRV14 sequence in the plasmid. In vitro transcripts are then used to transfect HeLa cells (Mizutani & Colonno, J. Virol., 56:628–632, 1985), ideally resulting in production of live chimeric viruses.

Once viruses have been produced, antibodies against the chimeric region can be used to screen potentially mutagenized viruses for incorporation of desired antigens. This can be done most advantageously as an immunoselection, for example, by immobilizing the antibody on microtiter plates, and adding virus-containing samples to the wells. The non-immune reactive viruses are then easily washed away.

Where populations of chimeric DNAs have been produced, it is most advantageouse to carry out all of the foregoing procedures on the mixture of DNAs, to produce a mixture of viruses. Once immune reactive viruses have been obtained, individual viruses can then be isolated, for example, by picking plaques from monolayers of HeLa cells treated with a dilute solution of virus. The virus from each plaque can then be amplified, and analyzed immunologically.

The amplification of single plaques to milligram quantities of virus is best done in a serial fashion, inoculating cells in monolayers with low multiplicities of infection. When the number of monolayers becomes unwieldy, it is most efficient to switch to suspension cultures for large scale propagations, though the relative yields are reduced. When plaques cannot be obtained, infected cells can either be harvested and chimeric viruses released by multiple freeze/thaw cycles, or, if necessary, the infected cells can be passaged until a variant of the virus succeeds in making plaques. When plaques can be obtained, but are difficult to amplify to high titer, it may be necessary to 1) repeat the mutagenesis using an oligomer with different codon-usage properties, 2) perform propagations in slower growing monolayers of cells, or 3) select for natural variants of the chimera that grow more easily (i.e., that produce larger plaques). Correctness of the most interesting constructions are determined by DNA sequencing of plasmid DNAs (Sanger, et al., Proc. Natl. Acad. Sci. U.S.A., 74:5463–5467, 1977) and by RNA sequencing of chimeric viruses (e.g., Rico-Hesse, et al. Virology, 160:311–322, 1987).

The cellular immune response also plays an extremely important role in providing immunity against viruses and other pathogens. Among the components of cell-mediated immune (CMI) response are cytotoxic T-lymphocytes (CTLs), macrophages, and so forth. Chimeric rhinoviruses will also stimulate the cellular immune system in relevant ways that will be beneficial in providing immunity against foreign pathogens. The determinants for optimal stimulation of cellular immunity are less well characterized than for those of the humoral immune response. It is anticipated that T-cell epitopes of foreign pathogens (and other sequences that provoke CMI) can be successfully placed in many portions of the HRV coat proteins in addition to the surface exposed regions. For this purpose, epitopes that provoke CMI can also be inserted into any of the non-structural proteins of the chimeric HRV, such as the polymerase (3D protein) or protease (3C protein) that are also produced in high copy number during infection in the host.

A further advantage of using HRV chimeras for immunization is that 90% of all rhinoviral serotypes ("major" group HRVs) bind to the intercellular adhesion molecule-1 (ICAM-1), which is expressed on many cell types. Along these lines, a particularly useful HRV having ICAM-1 receptor specificity is HRV-14. Among advantages for using HRV14 include the availability of a full-length clone, knowledge of the three-dimensional structure of HRV14 (Rossmann, et al., Nature, 317:145–153, 1985; Arnold & Rossmann, J. Mol. Biol., 211:763–801, 1990), and the extensive description of the HRV14 immunogenic surface (Rossmann, et al., ibid, 1985; Sherry, et al., J. Virol., 57:246–257 1986). The other 10% of HRV serotypes ("minor" group HRVs) bind to an, as yet, unspecified cellular receptor. Modification of these HRVs using the methodology of the invention for HRV14 would also yield chimeric vaccines. Examples of minor group HRVs which have been well characterized could be used in the present invention to produce chimeric rhinoviruses are HRV1A, whose structure has been determined (J. Mol. Biol., 210:91–111, 1989), and HRV2.

One of the tremendous advantages of using chimeric HRVs as vaccines is that multiple serotypes can be utilized. Thus, if immunity exists or develops to a given serotype, it is possible to use another chimeric HRV from a serotype for which there is no preexisting immunity. There have been at least 100 distinct HRV serotypes identified. Consequently, vaccination can be accomplished for an enormous variety of pathogens in a single individual. This is in sharp contrast to poliovirus, where only three serotypes exist. It is anticipated that eventually all HRVs could be potentially used successfully in this type of strategy (both the major and the minor group HRVs). Furthermore, since each serotype can carry multiple foreign epitopes, the possible arrangements of the epitopes are great. It is likely that simultaneous inoculation of an individual with multiple chimeric HRVs of even a single serotype can successfully immunize against multiple pathogens.

It may be especially advantageous to utilize recombinant chimeric human rhinoviruses when the chimeric portion is a hapten which ordinarily must be coupled to a less effective and sometimes problematic carrier molecule in order to confer immunogenicity. Such recombinant rhinoviruses having the chimeric region on their surface would, by themselves, effectively present this portion in a manner which renders it immunogenic and thereby eliminate the need for such coupling reactions. It should be emphasized that the chimeric region is typically engineered to be in a location of the rhinovirus that, under normal conditions, is immunogenic.

Any epitope, usually of proteinaceous origin, from a source which is capable of inducing an immune response specific to the source can potentially be used in the recombinant chimeric human rhinoviruses of the invention. In order to be effective as a vaccine, the foreign epitope present on the surface of the chimeric rhinovirus should be presented in an immunopotent manner such that components of the host immune system, such as T-cells or B-cells, are stimulated. However, as stated previously, the cellular immune response may be stimulated by foreign peptide sequences inserted at any region of the HRV proteins (coat proteins or otherwise), regardless of surface exposure.

Useful antigens for substitution in the recombinant chimeric human rhinoviruses can be identified by various criteria, such as the involvement of the antigen in neutralization of pathogenic infectivity, type or group specificity, recognition by patient antisera, and/or the presence of protective effects of antisera generated to the antigen. Desirably, an epitope derived from the antigen would display minimal antigenic variation with time. The genetic sequence encoding the epitope constituting the chimeric region of the chimeric rhinovirus may be obtained by techniques known to those of skill in the art such as by recombinant DNA techniques for plasmid DNA or cDNA reverse transcribed from genomic viral RNA or by chemical synthesis.

The recombinant chimeric human rhinoviruses have potential uses as vaccines for diseases and disorders wherein the source of the chimeric region is derived from a viral, neoplastic, parasitic, or bacterial source. Numerous viral-specific antigens are known to those of skill in the art and can potentially be incorporated into the chimeric rhinoviral vaccines of the invention. For example, such antigens, or portions thereof, which encode the epitope(s) include such sources as influenza A hemagglutinin; hepatitis A virus VP1 and VP3; hepatitis B surface, core, or E antigens; poliovirus capsid protein VP1, VP2, and VP3; rabies virus glycoprotein; retroviral envelope glycoproteins or capsid proteins; foot and mouth disease virus VP1; herpes simplex virus glycoprotein D; Epstein-Barr virus glycoprotein; pseudorabies virus glycoproteins; vesicular stomatitis virus glycoprotein, to name a few. Bacterial antigens that can be incorporated include those from the genera Pneumococcus, Salmonella, Shigella, Clostridia, Pseudomonas, Streptococcus, Staphylococcus, and Neisseria, to name a few. Parasitic antigens that can be presented on the chimeric rhinoviruses include those from the genera Trypanosoma, Leishmania, Plasmodium, and Toxoplasma, to name a few. Neoplastic antigens that can be displayed on the chimeric rhinoviruses include those from tumors and carcinomas (e.g., mammary, colon) and those from oncogene products or mutated oncogene products (e.g., ras, myc).

Human rhinovirus 14 (HRV14), and other HRV serotypes, are called common cold viruses because they are among the most commonly isolated viruses from humans experiencing mild respiratory illness. The virus is composed of 60 protomers related by icosahedral symmetry, each containing a single copy of each of four polypeptide chains VP1, VP2, VP3, and VP4. A single, positive strand of RNA, which is translated into a single precursor and then processed into its structural and functional components, is surrounded by the protein capsid. The three-dimensional structure of the HRV14 capsid has been solved (Rossmann, et al., Nature, 317:145–153, 1985) and refined (Arnold & Rossmann, Acta Cryst., A44:270–282, 1988) at 3.0 Å resolution by X-ray crystallography.

The complete nucleotide sequence of HRV14 is known (Stanway, et al., Nucl. Acids Res., 12:7859–7875,1984; Callahan, et al., Proc. Natl. Acad. Sci. U.S., 82:732–736, 1985). The major coat proteins, VP1, VP2, and VP3, form the surface of the virion and are recognized by the immune system. Structurally, these proteins are very similar to one another (Rossmann, et al., Nature, 317:145–153, 1985) sharing a common 8-stranded β-barrel structure. The differences among the coat proteins are manifested almost exclusively as loops with an irregular secondary structure that embellish the basic β-barrel motif where the neutralizing immunogenic sites are located primarily in these loops.

HRV14 has four neutralizing immunogenic sites defined by the locations of amino acid changes that enable the virus to escape neutralization by antibodies (Rossmann, et al., Nature, 317:145–153, 1985; Sherry & Rueckert, J. Virol., 53:137–143 (1985); Sherry, et al., J. Virol., 57:246–257, 1986). These neutralizing immunogenic sites, abbreviated NIms, designate the viral coat protein from which they are primarily derived. Thus, NIm-IA and NIm-IB are located primarily on VP1, and NIm-II, and NIm-III are located primarily on VP2 and VP3, respectively.

Human rhinoviruses have major advantages as vaccine vehicles over those that are currently in use. Rhinoviral pathology is typically mild (as shown in thousands of experimental infections in humans) and HRVs are high molecular weight carriers of multiple immunogenic sites capable of replicating in the host and provoking a high titer antibody response. The HRV14 serotype is particularly useful since this system offers: a high resolution three-dimensional refined structure; a well mapped immunogenic surface; and availability of a cDNA clone. The suitability of HRV14 for chimeric virus construction is illustrated herein by examples showing the successful construction of an HRV14:poliovirus 3 Sabin chimera (substituted at NIm-IA), an HRV14:influenza hemagglutinin chimera (substituted at NIm-II), and numerous HRV14:HIV-1 chimeras (substituted at NIm-II).

Since the rules of protein folding, assembly of macromolecules, and immune recognition and function are not yet known, the viability, antigenicity, and immunogenicity of recombinant chimeric human rhinoviruses could not be assumed prior to a clear demonstration of their construction. This work has demonstrated conclusively for the first time that it is possible to create chimeric HRVs that grow well and have potent antigenicity and immunogenicity profiles, making them excellent candidates for vaccine development.

Preferred in the present invention for stimulation of the humoral immune response are chimeric rhinoviruses wherein the chimeric portion is located at one or more of the four known distinct neutralizing immunogenic sites of the rhinovirus. More than one chimeric region may be substituted, thereby allowing a broader repertoire of stimulation of the immune system. Especially preferred, based on studies thus far, are chimeric substitutions occurring at the NIm-IA and NIm-II sites, since these sites display greater natural sequence variability among natural isolates than the NIm-IB and NIm-III sites and are therefore expected to more easily allow substitutions.

As previously stated, the size of the substituted chimeric region should be sufficient to induce an immune response in the host, but not of a size or of a chemical nature which would prevent proliferation of the virus or cause disruption of the virus. The substituted chimeric region is usually from about 5 to about 300 amino acids, preferably from about 5 to about 50 amino acids, most preferably, from about 5 to about 30 amino acids. In selecting chimeric regions for substitution, it should also be kept in mind that the optimal size of the chimeric region, at least in terms of substitutions made at the neutralizing immunogenic sites, may vary somewhat with a particular site. The substituted chimeric region may consist of non-contiguous segments of amino acids as do some of the native NIm sites.

It should be noted that for some of the larger substitutions, it is possible for a relatively small segment of the rhinovirus surface (for example, 5–20 amino acids) to be replaced by or given an insertion of as much as several hundred amino acid residues. Alternatively, an expression system such as baculovirus could be used to generate non-infectious empty capsids that are useful in immunization (Urakawa, et al., J. Gen. Virol., 70:1453–1463, 1989). The use of this latter system to produce the chimeric HRVs of the present invention could be especially valuable since generation of large quantities of vaccine material would not depend upon the compatibility of the foreign sequences with HRV reproduction requirements.

Table 1 lists various surface-exposed regions of the various NIm sites, as well as other surface regions, that will tolerate replacement or insertion of native sequences with chimeric sequences. The choices of residues defining a region, or region to be replaced or given insertions, are approximate, based on a combination of quantitative structural assignments (such as those corresponding to secondary structural elements) and an understanding of the HRV14 structure. Optimal replacements or insertions depend on the desired application. The listed nomenclature follows that of Rossmann, et al., (Nature, 317:145–153, 1985) and Arnold and Rossmann (J. Mol. Biol., 211:763 801, 1990). Residues in the viral proteins have been enumerated XYYY, where X corresponds to the viral protein number (VPX) and YYY the residue number within chain X.

The specific chimeras described in the examples involve alteration of the NIm-IA and NIm-II regions of HRV14. While the NIm-IB and NIm-III regions of the virus also have variable amino acid composition (as one would expect for immunogenic sites), the sequence alignments reveal less variation in chain lengths for these regions in different picornaviruses. On the other hand, the NIm-IA and NIm-II regions are characterized by diversity for both amino acid sequence and chain length, suggesting that they would be more likely to accommodate a greater variety of foreign sequences than either NIm-IB or NIm-III. However, it is anticipated that the majority of the surface of HRV14 is immunogenic when used for chimeric constructs of the nature described herein.

Amino acid sequence and computer graphic analysis of the neutralizing immunogenic site II (NIm-II) indicated that a protruding loop comprising amino acids

TABLE 1

| CANDIDATE SURFACE-EXPOSED HRV14 REGIONS FOR PLACEMENT OF CHIMERIC REGIONS | | | | | |
|---|---|---|---|---|---|
| | LOCATIONS OF ESCAPE MUTATIONS | RESIDUES IN REGION | LARGE | RESIDUES REPLACED INTERMEDIATE | SMALL |
| I. NIm sites | | | | | |
| A. NIm-IA | 1091,1095 | 1082–1099 | 1082–1099 | 1085–1096 | 1091–1095 |
| B. NIm-IB | 1083,1085 | 1079–1089 | 1079–1089 | 1081–1087 | 1082–1086 |
| | 1138,1139 | 1134–1143 | 1134–1143 | 1135–1141 | 1136–1140 |
| C. NIm-II | 2158,2159,2161,2162 | 2155–2169 | 2155–2169 | 2157–2165 | 2158–2162 |
| | 2 | 2132–2140 | — | 2132–2140 | 2134–2138 |
| | 2136 | 1206–1214 | — | 1206–1214 | 1208–1212 |
| | 1210 | | | | |
| D. NIm-III | 3072,3075,3078 | 3068–3082 | 3068–3082 | 3070–3080 | 3072–3078 |
| | 3203 | 3199–3207 | — | 3199–3207 | 3201–3205 |
| | 1287 | 1283–1289 | — | 1283–1288 | 1284–1288 |

TABLE 1-continued

CANDIDATE SURFACE-EXPOSED HRV14 REGIONS FOR PLACEMENT OF CHIMERIC REGIONS

| | LOCATIONS OF ESCAPE MUTATIONS | RESIDUES IN REGION | LARGE | RESIDUES REPLACED INTERMEDIATE | SMALL |
|---|---|---|---|---|---|
| II. Other surface regions | | | | | |
| A. VP3 "knob" | — | 3053–3069 | 3053–3069 | 3057–3065 | 3058–3062 |
| B. FMDV loop | — | 1200–1221 | 1200–1221 | 1206–1214 | 1208–1212 |
| C. VP2 BC loop | — | 2070–2078 | — | 2070–2078 | 2072–2076 |
| D. VP1 C-terminus | — | 1255–1289 | 1255–1289 | 1265–1280 | 1270–1275 |
| E. VP2 C-terminus | — | 2254–2262 | — | 2254–2262 | 2258–2262 |
| F. VP3 C-terminus | — | 3222–3236 | — | 3227–3236 | 3230–3236 |

157–166 of VP2 on HRV14 would be an ideal candidate for replacement by foreign antigens. A chimeric virus containing an influenza hemagglutinin (HA) immunogenic sequence in the place of the NIm-II loop was constructed by applying recombinant DNA techniques to a plasmid containing a cDNA representation of the full-length HRV14 genome. The resulting chimeric HRV14:influenza HA (HRV14:HA) was tested for loss of Nim-II antigenicity and for introduction of influenza antigenicity. As expected, monoclonal antibodies directed against the NIm-II site of HRV14 do not neutralize HRV14:HA, which indicates that there is loss of recognition of this site. Neutralization tests performed with polyclonal antisera against four relevant strains of influenza HA show that three of the four antisera have significant, even moderate (reciprocal neutralizing titers of 30–300), neutralizing activity on the HRV14:HA chimera.

The escape mutations that define the NIm-IA site (VPI residues 91 and 95) are found within a 14-amino acid structural unit that can be classified as an ω-loop (Leszczynski & Rose, Science, 234: 849–855, 1986) which pinches together at its termini. The NIM-IA loop is relatively compact and self-contained, and the majority of the short contacts that it has with the rest of the capsid occur in the terminal residues. This, together with the fact that the loop termini form a piece of the conserved β-barrel structure, suggests that these termini function as "anchor points" onto which foreign stretches of peptide may be introduced without greatly perturbing the function of the virus. The Nim-II site has a more complex structure than the NIm-IA loop and is a discontinuous epitope. The escape mutations that define the NIm-II site (VP2 residues 158, 159, 161, 162, and 135, and VPI residue 210) are located on three non-contiguous stretches of peptide in the VP2 and VP1 proteins (Rossmann, et al, ibid, 1985; Sherry, et al., J. Virol., 57:246 257, 1986). The highest density of escape mutations in NIm-II occurs on a loop that includes residues 150 to 168 of VP2. Structure and sequence information suggests that VP2 Ser 157 (directly preceding the escape mutations) and VP2 Pro 165 (following the escape mutations and well-conserved among polioviruses, Coxsackie viruses, and rhinoviruses) serve as "anchor points" for the modular replacement of intervening amino acids. Alignments of NIm-II of HRV14 with other rhinoviruses and polioviruses indicated that at least seven more amino acids could be tolerated in this region than are present in HRV14, and thus large immunogenic insertions would be possible at this location. For example, we have found that at least 17 amino acids can be inserted into the NIM-II loop described. However, compensatory changes may have to be considered in the neighboring protein environment in some of the chimeric constructs to enable the viral protein shell to fold and function properly. By taking advantage of the knowledge of the three-dimensional structure of HRV14 and, wherever possible, that of the transplanted antigens, it is possible to avoid grafting sequences blindly into important structural elements that could disrupt the functions of the virus or result in poor antigen presentation.

The NIm-III and NIm-IB sites are also discontinuous epitopes. The escape mutations defining the NIm-III site (VP3 residues 72, 75, 78, and 203, and VP1 residue 287) are located in three distinct polypeptide segments that are spatially adjacent. The escape mutations that define the NIm-IB site (VP1 residues 83, 85, 138, and 139) are located on two adjacent polypeptide segments in a protruding region near the five-fold axis of icosahedral symmetry of the rhinovirus. While the length and composition of NIm-IB and NIm-III in different picornaviruses are more conserved than for NIm-IA and NIm-II, each of the NIm sites is favorable for replacement in constructing the chimeric HRVs of the invention.

In an embodiment illustrated herein, a chimeric virus was successfully produced by recombinant modification of a human rhinovirus (HRV14) in which the NIm-II loop was replaced with a neutralizing immunogen from the orthomyxovirus, influenza virus. In this instance, the immunogen was selected from the influenza hemagglutinin which naturally bears a conformational resemblance to one of the prominent loops of the NIm-II transplantation site of HRV14. It was thought that selecting such a region would enhance the likelihood that the influenza HA sequence would adopt a conformation recognizable by and capable of inducing, neutralizing antibodies against influenza. This sequence was also of special interest because it is located at the periphery of the sialic-acid binding pocket of influenza HA that is believed to be involved in receptor attachment. The HRV14:HA chimera was generated based on the mutagenesis methods of Kunkel, et al. (Meth. Enzymol., 154:367–381, 1987). The resulting chimeric HRV14:influenza HA was tested for loss of NIm-II antigenicity and for introduction of influenza antigenicity and growth characteristics.

In other specifically exemplified embodiments of the invention, an antigenic segment of a picornavirus was substituted at an alternate immunogenic neutralization site of HRV. In this case, the NIm-IA loop of HRV14 was replaced by the N-Ag1 site of poliovirus.

In addition, the inventors have produced chimeric rhinoviruses displaying antigenic segments from human retroviruses as exemplified by HIV. The HIV chimeric rhinoviruses involve substitution of portions derived from the gp120 HIV-1 envelope glycoprotein. The HIV-1 chimeric regions are preferably substituted at the NIm-II site of HRV14.

For example, a primary target for vaccine design against human immunodeficiency virus type 1 (HIV-1) is the principal neutralizing domain, which has been mapped to the V3 loop of the gp120 envelope glycoprotein. (Goudsmit, J., et al., Proc. Natl. Acad. Sci. USA 85:4478-4482, 1988; Palker, T. J., et al., Proc. Natl. Acad. Sci. USA 85:1932-1936, 1988; Rusche, J. R., et al., Proc. Natl. Acad. Sci. USA 85:3198-3202, 1988). As discussed in more detail below, a chimeric HRV14:HIV-1 library has been produced in which V3 loop sequences corresponding to a relatively conserved segment and five varied amino acids were flanked by linkers or adapters of 0-2 randomized amino acids and transplanted onto the surface of HRV14. Two neutralizing anti-HIV-1 V3 loop monoclonal antibodies were then used to immunoselect those chimeras that presented their HIV-1 epitopes in conformations that mimic those of HIV-1. The immunoselected subset was propagated and purified to select chimeras with favorable growth and purification properties.

The chimeric rhinovirus to be used in this invention can be generated from a stable source of plasmid DNA, or later from seed stocks of the chimeric HRV. Using the techniques described, the recombinant chimeric human rhinoviruses generated will have the exact desired sequence content and length of amino acids and will not have any undesired amino acids that could result from using a restrictive mutagenesis cassette. When the chimeric HRV is to be produced in large amounts, large numbers of cells can be accommodated either in suspension cultures and/or on carriers such as microcarrier beads. Propagations can be performed in transformed human cells, such as the H1-HeLa cells used in this work, or preferably in non-transformed human cells, such as human diploid fibroblast cells (WI-38, MRC-5, etc.). Virus can be obtained in purified form from infected cells following cell lysis. Examples of purification steps include standard differential centrifugation techniques, concentration by ultrafiltration or pressure dialysis, or concentration by precipitation.

According to the present invention, a vaccine for stimulating an immune response to the chimeric region comprises a recombinant chimeric human rhinovirus and an inert pharmaceutically acceptable carrier or diluent. Preferably the carrier or diluent is one compatible with vaccine administration by mass administration techniques. However, the carrier or diluent may also be compatible with other administration methods such as injection, eye drops, nose drops, and the like.

The vaccine according to the present invention is administered in amounts sufficient to stimulate the immune system against the chimeric portion of the HRV. Preferably, the vaccine is administered in dosages ranging from about $10^2$ to about $10^8$ TCID$_{50}$, preferably from about $10^3$ to about $10^6$ TCID$_{50}$. Since the live chimeric virus replicates in the host, smaller doses may be possible.

The vaccine containing inactivated recombinant chimeric human rhinovirus according to the present invention is administered in amounts sufficient to stimulate the immune system against the chimeric portion of the virus. Preferably, the vaccine is administered in dosages ranging from about 10 ng to about 100 µg, preferably between about 100 ng to about 10 µg.

The chimeric rhinoviruses when used as a vaccine usually do not require adjuvants since HRV is a large molecular aggregate capable of stimulating a robust immune response on its own. However, if desired, the vaccines of the present invention may also contain one or more adjuvants. This is especially true when an inactive vaccine is utilized. Any suitable adjuvant can be used including chemical and polypeptide immunostimulants which enhance the response of the immune system to antigens. Preferably, adjuvants such as aluminum hydroxide, aluminum phosphate, plant and animal oils, and the like are administered with the vaccine in amounts sufficient to enhance the immune response to the chimeric portion of the recombinant HRV. The amount of adjuvant added to the vaccine will vary depending on the nature of the adjuvant, generally ranging from about 0.1 to about 100 times the weight of the recombinant chimeric human rhinovirus, preferably, from about 1 to about 10 times the weight of the recombinant chimeric human rhinovirus.

The vaccines of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate, and the like. A stabilizer is particularly advantageous when a dry vaccine preparation is prepared by lyophilization.

The vaccine can be administered by various routes including nasally, ophthalmically, by injection, by exposure, or by any suitable method. A vaccine containing inactivated recombinant chimeric human rhinovirus according to the present invention can be administered by injection. When administered by injection, the vaccines are preferably administered parenterally. Parenteral administration as used herein means administration by intravenous, subcutaneous, intramuscular, or intraperitoneal injection.

In proposing and discussing the use of human chimeric rhinoviruses as vaccines, we do not intend to limit the meaning of the word "vaccine". Vaccines are generally considered to be pharmaceutical formulations of viruses or parts thereof that when administered to a patient before infection by a pathogenic virus, can stimulate the body to produce antibodies against the pathogenic virus. However, although such antibodies can in some cases prevent the onset of the clinically recognized disease state, this need not necessarily be the case. Vaccines may, when administered to a patient before infection by a pathogenic virus, only slow down or otherwise inhibit, but not prevent, the patient from exhibiting clinical symptoms of infection. Furthermore, vaccines may be administered to a patient after infectionby a pathogenic virus, and to some extent stimulate the body's immune response against the infection. Thus, when we discuss the use of the chimeric rhinoviruses of the present invention, for example, as vaccines against HIV, we do not necessarily claim that such rhinoviruses can prevent AIDS in a patient treated therewith; we only suggest that treatment with the chimeric rhinovirus will slow or otherwise inhibit the onset of AIDS, at least to some extent. Alternatively, such chimeric rhinoviruses may be useful as immune stimulatory treatments for those individuals already infected with HIV.

An additional, important use for the chimeric rhinoviruses of the present invention is as antigens for use in diagnostic testing. Because the chimeric regions contain antigenic protein sequences from target organisms, and they become displayed on the surface of the rhinovirus in a manner well suited to recognition and binding by antibodies, they should be ideal for this purpose. This is particularly so in instances where a viral infection is being tested for. For example, methods for screening or testing patients to determine if they are infected with HIV generally rely upon testing for the presence of anti-HIV antibodies that have been produced by the body and are present in the blood of infected individuals. Chimeric rhinoviruses of the present invention that have HIV antigenic regions exposed on their surfaces should serve as ideal antigens for such diagnostic purposes. That they are able to serve such a utility is well demonstrated by the ability of such chimeric rhinoviruses to react with anti-HIV antibodies, as further described in the examples below.

While the disclosure above generally describes the present invention, a more complete understanding can be obtained by reference to the specific Examples which follow. The Examples are provided only for purposes of illustration and are not intended to limit the scope of the invention.

EXAMPLES

Materials and Methods

Wild-type HRV14 virus (Sherry & Rueckert, J. Virol. 53:137–143, 1985) and H1-HeLa cells (Lee, Monroe & Rueckert, J. Virol. 67:2110–2122, 1993) were obtained courtesy of Drs. R. R. Rueckert (University of Wisconsin) and M. G. Rossmann (Purdue University). Wild-type and chimeric viruses were grown in H1-HeLa cells, which are adapted for rhinovirus growth (Conant and Hamparian, J. Immunol., 100:107–113, 1968). Viruses were plaque-assayed using R-19 HeLa cells (Abraham and Colonno, J. Virol., 51:340–345, 1984). Mutagenesis was performed on a plasmid derived by inserting a full-length cDNA clone of HRV14 into the HindIII and HincII sites of the pBS phagemid (Stratagene Cloning Systems) to produce pWR40, a gift from W. M. Lee and R. R. Rueckert (Univ. of Wisconsin). The E. coli strains used for transformation and plasmid preparation were JM83 (Gene, 33:103–119, 1985) obtained from Dr. P. Maliga (Waksman Institute) and JS4 (Bio-Rad Laboratories).

Restriction enzymes ApaI, ClaI, SmaI, and T3 RNA polymerase were purchased from Bethesda Research Laboratory (BRL). T4 DNA polymerase was purchased from Boehringer Mannheim Biochemicals. T4 polynucleotide kinase was purchased from New England Biolabs. Ribonuclease inhibitor RNasin was obtained from Promega Corporation. Ribonucleotide triphosphates, deoxynucleotide triphosphates, and dideoxynucleotide triphosphates were purchased from Pharmacia LKB Biotechnology. Radioactive isotopes were obtained from NEN/DuPont.

Anti-HRV14 guinea pig serum was purchased from American Type Culture Collection (ATCC, NIAID v-103-501-558). Monoclonal antibodies against the HRV14 NIm-II site were gifts from A. G. Mosser and R. R. Rueckert (University of Wisconsin). Anti-influenza HA serum was a gift from Dr. R. Webster (St. Jude Children's Research Hospital, Memphis, Tenn.).

H9/FDA cells (Mann, D. L., et al., AIDS Res. Hum. Retroviruses 5:253–255, 1989) were used for propagation of HIV-1 (White-Scharf, et al., Virology 192:197–206, 1993). The HIV-1 strains used were MN (Gallo, R. C., et al., Science 224:500–503, 1984 and Shaw, G. M., et al; Science 226:1165–1170, 1984; NIH AIDS Research and Reference Reagent Program, from R. Gallo) and IIIB (Gallo, R. C., et al., Science 224:500–503, 1984) and ALA-1 (Englund, G., et al., Virology 181:150–157, 1991), from S. Zolla-Pazner. Medium M is MEM supplemented with 10 mM 4-(2-hydroxyethyl)-1piperazineethanesulfonic acid (HEPES), pH 7.3, 0.1 mM non-essential amino acids, 10 mM L-Gln, and 100 units/ml Penicillin-Streptomycin. PA medium is MEM supplemented with 20 mM HEPES, pH 7.3, 10 mM $MgCl_2$, 4 mM L-Gln, 100 units/ml Penicillin-Streptomycin, and 10% fetal bovine serum (FBS).

Example 1

Chimeric Rhinovirus Displaying Influenza Hemagglutinin Antigen

A chimera of HRV14 displaying an immunogen from influenza hemagglutinin (HA) was constructed via site-specific mutagenesis of the HRV14 cDNA clone pWR40. Single-stranded DNA generated from the HRV14 cDNA plasmid was hybridized to a single-stranded synthetic oligonucleotide that is complimentary at the NIm-II borders, but that encodes the influenza HA sequence.

A graphical representation of the refined coordinates of HR14 showed that a 10 amino acid loop corresponding to neutralizing immunogenic loop II (NIm-II), corresponding to VP2 residues 157–166, protrudes from the surface of the virus. Sequence alignment of picornaviruses revealed that this region is among the most highly variable portions of the capsid proteins, indicating a likelihood for accommodating foreign sequences without causing gross disruption of the viral capsid structure. The NIm-II structure on HRV14 represents a discontinuous epitope that includes segments of polypeptides from both VP2 and VP1. In this embodiment of the invention, the section of NIm-II that is both highly protruding from the virion surface and most highly exposed (Arnold & Rossmann, J. Mol. Biol., 211:763–801, 1990), and that contained the highest density of mutations in an analysis of spontaneously arising mutants of HRV14 that survive in the presence of monoclonal antibodies that react with NIm-II, was replaced with the chimeric sequence.

A crude conformational matching of this region with influenza hemagglutinin (HA) identified a similarly protruding immunogenic loop with some conformational resemblance. Notably, the two HA residues that did not match well conformationally were both glycines, characterized by conformational flexibility (and residues in common between the sequences).

| HRV14 | (157) | SSANEVGGP | (165) (SEQ ID NO:1) |
|---|---|---|---|
| Influenza HA | (128) | TGVTQNGGS | (136) (SEQ ID NO:2) |
| HRV14:influenza HA | | SGVTQNGGP (SEQ ID NO:3) | |

The mutagenesis also introduced two new unique restriction sites at the two ends of the NIm-II loop to simplify further modifications and characterization. The chimeric cDNA plasmid was then used as a template for in vitro synthesis of viral RNA as a source of virion production. Single plaques were recovered from transfected monolayers of HeLa cells and then amplified. The successful construction of the HRV14:HA NIm-II chimera demonstrates that the NIm-II site is a good target for engineering and replacement by foreign sequences and that substitutions at this site can be recognized by antibodies directed against the new chimeric sequence. The HRV14:HAN Im-II chimera has also been crystallized, emphasizing the high degree of homogeneity of the chimeric rhinovirus.

A. CONSTRUCTION OF PLASMID

Single-stranded DNA was produced from pWR40 based on the method of Kunkel (Proc. Natl. Acad. Sci., U.S.A., 82:488–492, 1985; Kunkel, et al., Meth. Enzymol., 154:367–382, 1987). A 50 nucleotide oligomer encoding the desired immunogenic sequence from the influenza hemagglutinin as well as two unique restriction sites (recognized by the enzymes ApaI and ClaI) was synthesized, deprotected, and further purified on an 8% polyacrylamide sequencing gel. The major and slowest migrating band was isolated and extracted (with 0.5M ammonium acetate, 1 mM EDTA overnight at 37° C.), precipitated in 70% ethanol and resuspended in TE buffer (10 mMTris-HCl, pH 7.4, 1 mM EDTA). Oligomer was phosphorylated in the presence of 100 mM Tris-HCl, pH 7.5, 10 mM $MgCl_2$, 1 mM DTT, 0.1 mM EDTA, 1 mM spermidine, 1 mg/ml BSA, 1 mM ATP, and 10 units of T4 polynucleotide kinase. Free nucleoside triphosphates were then removed using Sephadex G-25 (Pharmacia) in a Spin-X centrifuge filter unit (Costar).

Mutagenesis was performed by hybridizing 10 pmol of phosphorylated, mutagenic oligomer to 1 pmol of single-stranded pWR40 DNA, then synthesizing the second strand by adding 20 mM HEPES, pH 7.8, 2 mM DTT, 2 mM $MgCl_2$, 0.5 mM each of dATP, dCTP, dGTP, and dTTP, 1 mM ATP, 10 units of T4 DNA polymerase, and 400 units of T4 DNA ligase.

A small amount of the mutagenesis mixture was used to transform competent JM83 cells (method of Kushner in Maniatis, et al., Molecular Cloning, Cold Spring Harbor Laboratory, Cold Spring Harbor, N.Y., 1982). Isolated transformant colonies were grown in LB medium (Miller, Experiments in Molecular Genetics, Cold Spring Harbor Laboratory, Cold Spring Harbor, N.Y., 1972). Crude preparations of DNA were prepared by the method of Serghini, et al. (Nucleic Acids Res., 17:3604, 1989) and screened for correctness of size and restriction pattern. Apparently correct clones were subsequently prepared in larger and purer quantities (using Circle-Prep™, Bio 101) to provide substrates for DNA sequencing and in vitro transcription. DNA sequencing was performed using the Sanger dideoxy method (Sanger, et al., Proc. Natl. Acad. Sci., 74:5463 5467, 1977). RNA sequencing was performed using reverse transcription to generate DNAs that were subsequently sequenced.

The plasmid containing the influenza hemagglutinin neutralizing immunogen, pWR40:HA, was linearized outside of the HRV14-encoding sequence with the restriction enzyme SmaI to generate templates for in vitro transcription. According to the methods of Mizutani and Colonno (J. Virol., 56:628–632, 1985), 1 µg of DNA was incubated for 1 hour at 37° C. in the presence of 40 mM Tris-HCl 8 mM $MgCl_2$, 25 mM NaCl, 2 mM spermidine, 5 mM DTT, 2 mM each of the ribonucleoside triphosphates, 50 units of the ribonuclease inhibitor, RNAsin, and 250 units of T3 RNA polymerase (total volume of 50 µl ), yielding typically 50 µg of viral RNA transcripts. Formaldehyde agarose gel electrophoresis revealed a single band of RNAs of the expected length of 7.2 kb, corresponding to full-length genomic RNA.

B. PRODUCTION OF CHIMERIC VIRUSES

In vitro synthesized RNAs were prepared for transfection according to Mizutani and Colonno (ibid). After boiling at a variety of dilutions for 2 minutes in $H_2O$ and immediately placing on ice, samples of 12 µl were mixed with 400 µl of ice-cold IRA buffer (10 mM HEPES, pH 7.3, 0.14M UCI, 1 mM $MgCl_2$, and 1.2 mg/ml DEAE-dextran). 200 µl of each mixture were plated in duplicate on monolayers of H1-HeLa cells and incubated for 20 minutes at 34° C. The plates were then overlaid with 0.5% agar in PA medium and incubated at 34° C. for 72±6 hours. To visualize plaques, plates were stained with 0.03% Neutral Red-containing PBS and incubated at 34° C. for 1 hour. Infectious virus was recovered from plaques by picking them individually into 600 µl of PA medium with sterile pasteur pipettes and freezing and thawing rapidly three times. The specific infectivity was found to be about 500 plaque-forming units (PFU)/µg transcript. Plaque assays showed that, as for pWR40, a single plaque generated from pWR40:HA had $10^4$–$10^5$ PFU. Viruses from isolated plaques were amplified in HI-HeLa cells by the scheme shown in Table 2.

C. CHARACTERIZATION

A neutralization assay of HRV14 was performed in quadruplicate by mixing $10^4$ PFU of virus with various dilutions of antibodies in a 96 well microtitration plate and incubating at room temperature for 1 hour. $10^4$ H1-HeLa cells then were added into each well and incubated at 34° C. for 64–72 hours at which time each well was stained with 50 µl of 0.1% crystal violet for 10 minutes and washed twice with water. The neutralizing titer was defined as the reciprocal of the antibody dilution that corresponded to cytopathy of approximately 50% of the cell monolayers.

In order to determine the growth curve of HRV14, 2.5× $10^5$ H1-HeLa cells in 1 ml of M medium were seeded into a 2 $cm^2$ well of 24 well tissue culture plate (Cat #4550-03524, Bellco Biotechnology) and incubated at 34.5° C. in 0.5% $CO_2$ for 16 hours. Medium was aspirated off and 2.5×$10^5$ PFU (in 0.2 ml of M medium) of wild-type or chimeric virus were added onto the monolayers and plates were incubated at room temperature for 1 hour for viral attachment. Medium was aspirated off and monolayers washed with 0.5 ml of PBS. 1.0 ml of M medium was added into the well and then incubated for 0, 0.5, 1, 2, 4, 7, 10, 12, 16, and 24 hours. Medium was collected and the monolayer was washed with 0.125 ml of PBS. 1.25 ml of M.

TABLE 2

| | AMPLIFICATION OF HRV14:HA CHIMERIC VIRUS | | | | |
|---|---|---|---|---|---|
| STAGE OF | INOCULUM | | PROPAGATION TIME | TOTAL | FOLD |
| AMPLIFICATION | SOURCE | MOI[1] | (HOURS) | OUTPUT[2] | AMPLIFICATION |
| 1. single plaque | RNA transfection | — | 72 ± 6 | $10^4$–$10^5$ | — |
| 2. infected[3] | 50% of stock From | $10^{-4}$–$10^{-3}$ | 33–48 | $10^6$–$10^8$ | 500–1000 |

TABLE 2-continued

AMPLIFICATION OF HRV14:HA CHIMERIC VIRUS

| STAGE OF AMPLIFICATION | INOCULUM | | PROPAGATION TIME (HOURS) | TOTAL OUTPUT[2] | FOLD AMPLIFICATION |
|---|---|---|---|---|---|
| | SOURCE | MOI[1] | | | |
| monolayer 3. infected monolayers (10–15 150 mm dia. dishes, until 50–80% CPE observed) | (1.) 50% of stock from (2.) | $10^{-2}$–$10^{-1}$ | 33–48 | $10^9$–$10^{10}$ | 500–1000 |
| 4. suspension propagation[4] (for two viral multiplication cycles) | 25–50% of stock from (3.) | $10^{-1}$–$10^0$ | 23 | $10^{11}$ | 20–40 |
| 5. suspension propagation[4] (for two viral multiplication cycles) | 20–30% of stock from (4.) | 2–5 | 10.5 | $10^{11}$ | 3–5 |

[1]Multiplicity of infection
[2]Plaque-forming units (PFU)
[3]150 mm dia. dish; until primary cytopathic effect (CPE) observed
[4]In a 4 l Ehrlenmeyer flask Medium was then added into each well. Both the cell monolayer and growth medium were collected and frozen at −80° C. until they could be subsequently titered for virus production.

Immunologic assays were performed on the chimeric HRV14:HA wherein the influenza HA NIm site had been transplanted at the HRV14 NIm-II site. The chimera was tested by three groups of antibodies for their neutralizing activities (Table 3).

TABLE 3

ANTI-INFLUENZA HA SERA NEUTRALIZE CHIMERIC HRV14:HA BUT NOT NATIVE HRV14

| Antiserum | RECIPROCAL OF NEUTRALIZING TITERS[5] | |
|---|---|---|
| | Wild-Type HRV14 | Chimeric HRV14:HA |
| Anti-HRV14 serum #1 | 9,200 ± 1,100 (n = 7) | 8,300 ± 400 (n = 8) |
| Anti-HRV14 serum #2 | 68,800 ± 1,000 (n = 8) | 68,800 ± 1,000 (n = 8) |
| Anti-HRV14 serum #3 | 75,100 ± 2,200 (n = 8) | 59,100 ± 5,000 (n = 11) |
| Anti-NIm-II MAb #1 | 340 ± 35 (n = 6) | ≦14 ± 2 (n = 4) |
| Anti-NIm-II MAb #2 | 7,100 ± 50 (n = 6) | ≦8 ± 1 (n = 4) |
| Anti-Influ. HA serum #1 | ≦6 (n = 3) | 220 ± 40 (n = 16) |
| Anti-Influ. HA serum #2 | ≦6 (n = 3) | 180 ± 25 (n = 18) |
| Anti-Influ. HA serum #3 | ≦6 (n = 3) | 200 ± 70 (n = 20) |
| Anti-Influ. HA serum #4 | ≦6 (n = 3) | 330 ± 85 (n = 8) |

[5]The reciprocal of the antiserum dilution causing the viral cytopathic effect to decrease by 50%.

The chimeric HRV14:influenza HA was tested for loss of NIm-II immunogenicity and for introduction of influenza immunogenicity. Monoclonal antibodies directed against the NIm-II site of HRV14 either failed to neutralize HRV14:HA altogether, or showed only 3% residual neutralizing activity, which indicated that there was loss of recognition of this site. Neutralization tests performed with polyclonal antisera against four relevant strains of influenza HA showed significant, even moderate (reciprocal neutralizing titers of 30–300), neutralizing activity against the HRV14:HA chimera by three of the four antisera. Plaque reduction assays were also performed with the anti-influenza HA sera and showed similar results. These experimental results show that the influenza HA antigen has been expressed on the chimeric HRV14 surface and continues to be antigenic in this new context.

Example 2

Chimeric Rhinovirus Displaying Poliovirus Antigen

Using the basic techniques described in Example 1, a chimeric virus-encoding plasmid was constructed which utilized the immunodominant neutralizing epitope, N-Ag1, from poliovirus type 3 Sabin. This epitope was substituted for NIm-IA, the analogous site on HRV14. This alteration allowed the production of virions, thus demonstrating that the NIm-1A site may also be used as a target for immunogen replacement for the chimeric region.

This particular chimera was chosen because of the structural similarity of the capsid proteins and sequence similarity of the two viruses. As in the case of the HRV14:HA chimera, the HRV14:poliovirus 3 Sabin chimera was generated based on the mutagenesis method of Kunkel (Kunkel, et al. Proc. Natl. Acad. Sci., U.S.A., 82:488–492, 1985; Meth. Enzymol., 154:367–381, 1987). However, in this construct the immunogen was replaced on the surface of VP1 (shown in brackets below), including the residues that define the NIm-IA site. The type 3 sequence was chosen for this construct, since cases of type 2 and 3 poliomyelitis still occur.

| HRV14 | IQN | KDATGIDNHREA | KLF (SEQ ID NO:4) |
|---|---|---|---|
| polio 3 Sabin | VDN | EQPTTRAQ | KLF (SEQ ID NO:5) |

-continued

| polio 2 Lansing | VDN | DAPTKRAS | KLF (SEQ ID NO:6) |
| HRV14:polio 3 Sabin | IQN | EQPTTRAQ | KLF (SEQ ID NO:7) |
| HRV14:polio 2 Lansing | IQN | DAPTKRAS | KLF (SEQ ID NO:8) |

The site-specific mutagenesis method used involved the hybridization of single-stranded pWR40 DNA with a mutagenic DNA oligomer encoding the N-Ag1 loop of poliovirus 3 Sabin. After complete synthesis of the second strand, plasmids were ligated and used for transformation of the JM83 strain of *E. coli*. The plasmid DNAs from 50 transformant colonies were isolated and analyzed by restriction enzyme analysis. Correctness of plasmid and fragment sizes and the presence of a deliberately introduced unique ApaI restriction site in the polio N-Ag1 DNA were used to identify two apparently correct DNA representations of this chimera. More highly purified DNA samples of both of the recombinant plasmids were prepared and used for DNA sequencing as well as for templates for in vitro transcription following their linearization with the restriction enzyme SacI. The RNAs obtained were then used to transfect H1-HeLa cells. For both apparently correct DNA constructs, virus plaques were isolated. Preliminary experiments with polyclonal antisera directed against poliovirus 3 Sabin (American Type Culture Collection) indicated that the antisera specifically cause neutralization of the HRV14:polio 3 Sabin construct without causing non-specific neutralization of wild-type HRV14.

Example 3

Chimeric Human Rhinovirus 14:Human Immunodeficiency Virus Type 1 V3 Loop Seroprevalence Library

A. CONSTRUCTION OF HRV14:HIV-1 V3 LOOP SEROPREVALENCE LIBRARY

A library of chimeric HRV14:HIV-1 viruses was designed that would display many V3 loop sequences in a vast array of conformations. The site chosen for insertion was the major immunogenic portion of the NIm-II site of HRV14, loop 2 of the VP2 puff. Asn 160 was removed and amino acid residues were inserted between Ala 159 and Glu 161 (Table 4).

The central element of the V3 loop sequence is an invariant core sequence, IGPGRAF SEQ ID NO. 23, represented in 53% of 354 HIV-1 isolates predominantly from North America and Europe (LaRosa, G. J., et al., Science 249:932–935, 1991 and Myers, G., et al., Human Retroviruses and AIDS, 1991, Los Alamos National Laboratories, Los Alamos, New Mexico). Adjacent to this HIV-1 core are five residues that were represented in proportion to their seroprevalence among these isolates. The six residues most commonly found in the position N terminal to the invariant core (His, Thr, Pro, Arg, Asn, and Ser) represented 93% of amino acids found at this position. Likewise, the amino acids chosen for the four positions C terminal to the HIV core represented 89–97% of amino acids for each of these positions. Zero to two completely randomized positions were engineered on each side of the HIV-1 insert resulting in $2.7 \times 10^8$ possible unique members associated with a vast array of lengths.

TABLE 4

| | | | Amino acid sequences of NIm-II inserts[6] | | | | |
|---|---|---|---|---|---|---|---|
| | Varied HIV-1 sequences | HIV-1 core | Varied HIV-1 sequences | | | | |
| Linker | 93% | 53% | 95% | 94% | 97% | 89% | Linker |
| XX | H(50/45) | IGPGRAF | Y(80/72) | T(55/60) | T(88/81) | G(75/81) | XX |
| X  | T(10/5)  |         | V(6/1)   | A(39/40) | A(4/9)   | E(6/9)   | XX |
| —  | P(10/15) |         | H(5/9)   |          | I(4/5)   | R(4/9)   | XX |
| XX | R(10/15) |         | F(2/8)   |          | R(1/4)   | K(4/1)   | X  |
| X  | N(7/15)  |         | L(2/1)   |          | G(0/0.5) |          | X  |
| —  | S(6/5)   |         | D(0.3/9) |          | V(0/0.5) |          | X  |
| XX |          |         |          |          |          |          | —  |
| X  |          |         |          |          |          |          | —  |

[6]The approximate percentages of sequenced HIV-1 isolates containing any of the residues encoded are shown. In Parentheses, the first number corresponds to the percentage among the 354 known sequences; the second number corresponds to the percentage encoded in the HRV14:HIV-1 library.

sequences, and conformations.

Mutagenesis was performed with the p3IIST plasmid (Smith, A. D., et al., J. Virol. 68:575–579, 1994). Cassettes encoding HIV-1 V3 loop sequences, the flanking randomized amino acids, and ApaI and ClaI sites were generated by hybridizing oligonucleotides complementary at their 3' ends and completing second strand synthesis. To generate amino acids in proportion to their observed distributions, the phosphoramidites used for DNA synthesis were mixed in ratios calculated to yield the desired codon frequencies (Table 4). Cassettes were digested with ApaI and ClaI and ligated to dephosphorylated ApaI-ClaI-digested p3IIST.

B. GENERATION OF CHIMERIC VIRUSES

The ligated products were electroporated into *E. coli* with a Gene Pulser System (Bio-Rad Laboratories). Transformed cells were grown in liquid cultures and the mutagenized plasmids were isolated in pools. The plasmids were used for in vitro transcription and transfection reactions (Mizutani, S. & Colonno, R. J., J. Virol. 56:628–632, 1985). Viable chimeric viruses were obtained from H1-HeLa cell cultures exhibiting cytopathic effects (CPE).

C. SCREENING OF LIBRARY WITH MONOCLONAL ANTIBODIES THAT NEUTRALIZE HIV-1

Chimeric viruses were captured on microtiter plates (Nunc Immunosorb) coated with 40 μl of 0.1 mg/ml of mouse monoclonal antibody (MuMLAb) NM-01 (Ohno, T., et al., Proc. Natl. Acad. Sci. USA 88:10726–10729, 1991, from M. Terada) or human monoclonal antibody (HuMAb) 694/98-D (Gorny, M. K., et al., J. Virol. 66:7538–7542, 1992, from M. Gorny and S. Zolla-Pazner) in 50 mM sodium borate, pH 8.5. After an overnight incubation at room temperature, the plates were blocked with 3% gelatin in phosphate buffered saline (PBS) for 1 hr at 37° C. and then washed with PBS containing 0.05% Tween-20 (PBS-T). $2.5 \times 10^4$ plaque forming units (PFU) of chimeric HRV14:HIV-1 were added to each well in 25 µl PBS-T with 20% normal goat serum. After a 1 hr incubation at room temperature, the plates were washed with PBS-T followed by PBS alone. $2 \times 10^4$ H1-HeLa cells in 200 µl Medium M with 10% FBS were added to each well. Plates were incubated at 34.5° C. and 2.5% $CO_2$ until cells exhibited 60–100% CPE (~72 hrs) after which they underwent three cycles of freezing (–80° C.) and thawing (23° C.).

D. PROPAGATION, PURIFICATION, AND SEQUENCING OF IMMUNOCAPTURED CHIMERIC VIRUSES

Immunoselected and purified chimeric viruses were plaque-purified twice, harvested by three cycles of freezing and thawing, and used to infect H1-HeLa cells, yielding passage 1, or P1, viruses. P2 viruses derived from the subsequent passage were used as inocula for further propagations. Viruses were purified by differential high speed centrifugation (Zhang, A., et al., J. Mol. Biol. 230:857–867, 1993). Five chimeras, D6-4, DN-1, DN-6, DN-7, and DN-9, were characterized following immunoselection with MuMAb NM-01. D6-4 was also obtained following immunoselection with HuMAb 694/98-D. The mutagenized regions of the viral RNA from each chimeric virus were sequenced and found to be the same after their first (P1) and third (P3) passages; the sequences obtained are shown in Table 5, aligned with the relevant sequences of various HIV-1 strains for comparison. PCR products derived from cDNA copies of the vital RNA were sequenced using standard techniques.

E. PLAQUE REDUCTION ASSAYS USING NEUTRALIZING ANTI-HIV-1 ANTIBODY PREPARATIONS

Chimeric viruses were incubated with diluted antibody preparations for 1 hr at room temperature and added to H1-HeLa cell monolayers (25 PFU with antibodies/$1.8 \times 10^6$ cells). After 1 hr at 34.5° C. and 2.5% $CO_2$, they were overlaid with 0.5% agar Noble (Difco) in PA medium and incubated for 72 hrs. Anti-HIV-1 antibody preparations used were MuMAb NM-01, HuMAb 694/98-D, MuMAbs 59.1 (White-Scharf, M. E., et al., Virology 192:197–206, 1993 and Ghiara, J., B., et al., Science 264:82–85, 1994) and 50.1 (White-Scharf, M. E., et al., Virology 192:197–206, 1993 and Rini, J. M., et al., Proc. Natl. Acad. Sci. USA 90:6325–6329, 1993), from A. Profy, Repligen Corporation, polyclonal antibodies (PAbs) anti-MN octamer p200M and anti-IIIB octamer p127 (Wang, C. Y., et al., Science 254:285–288, 1991, from M. Li and C. Y. Wang, United Biomedical, Inc.), and MuMAb 0.5β (Matsushita, S., et al., J. Virol.62:2107–2114, 1988, from A. Profy, Repligen Corporation).

Five neutralizing anti-HIV-1 antibody preparations were each able to neutralize all five chimeric viruses in plaque reduction assays (Table 6).

TABLE 5

V3 LOOP SEQUENCES[7]

HIV-1 Peptide Sequences (strain clade):

| | |
|---|---|
| MN, B | ESVQINCTRPNYNKRKRIHI . .GPGRAFYTTKNM[8](SEQ ID NO:9) |
| IIIB,B | QSVEINCTRPNNNTRKSIR - QR - - - - - - VTIGKI[8](SEQ ID NO:10) |
| SF2,B | KSIY - . .- - - - - -HTTG[9](SEQ ID NO:11) |
| SC,B | EAVEINCTRPNNNTIKSIH - . .- - - - - -YATGDM[10](SEQ ID NO:12) |
| WMJ2,B | ESVEINCTRPYNNVRRSLS - . .- - - - - -.RTREM[10](SEQ ID NO:13) |
| Uganda, D | ESVTINCTRPYSNTRQGTH - . .- - - - - -YCTSGYM[10](SEQ ID NO:14) |
| Thai, B | ESVEINCTRPNNNTRKSIHL . .- - -Q-WYTTGQM[10](SEQ ID NO:15) |
| Brazil,B | ESVVINCTRHNNNTRKSIHV . .-W- -SLFTTGEM[10](SEQ ID NO:16) |
| RF,B | KSITK . . - - - -VIYATG[9](SEQ ID NO:17) |

Chimeric Virus Sequences:

| | |
|---|---|
| D6-4 | P - . .- - - - - -DATER(SEQ ID NO:18) |
| DN-1 | H - . .- - - - - -HATES(SEQ ID NO:19) |
| DN-6 | P - . .- - - - - -YATEH(SEQ ID NO:20) |
| DN-7 | P - . .- - - - - -HATGE(SEQ ID NO:21) |
| DN-9 | P - . .- - - - - -HVTE(SEQ ID NO:22) |

[7]Dashes represent conserved residues in the common HIV-1 IGPGRAF core. Residues at randomized positions of the chimeric virus inserts are in boldface type.
[8]Wang, C. Y., et al., Science 254:285–288, 1991.
[9]NIH, AIDS Research and Reference Reagent Program, Division of AIDS, NIAID, NIH. 1993.
[10]Peptides were synthesized as radial octamers using the Merrifield solid-phase method at United Biomedical, Inc. (as described in Wang et al., cited in footnote 8.)

TABLE 6

| Chimeric virus | Nlm-II insert | Sequences and antigenicity of selected chimeras[11] MuMAb NM01 (ng/ml) | HuMAb 694/98-D (ng/ml) | MuMAb 59.1 (ng/ml) | PAb anti-MN octamer (l/dilution) | PAb anti-IIIB octamer (l/dilution) |
|---|---|---|---|---|---|---|
| D6-4 | P::::::DATE R (SEQ ID NO:18) | 9.1 | 41 | 53.8 | 23,400 | 66,700 |
| DN-1 | H::::::HATE S (SEQ ID NO:19) | 3.0 | 6.5 | 2.1 | 408,700 | 89,700 |
| DN-7 | P::::::YATE H (SEQ ID NO:20) | 6.9 | 4.7 | 4.7 | 78,800 | 34,000 |
| DN-6 | P::::::HATG E (SEQ ID NO:21) | 2.1 | 160 | 3.6 | 177,600 | 40,100 |
| DN-9 | P::::::HVTE (SEQ ID NO:22) | 3.0 | 250 | 3.9 | 21,500 | 86,700 |

[11]Chimeric virus plaque reduction titers are expressed as the concentrations or dilutions of antibody preparations corresponding to a 50% reduction in the number of plaques.

MuMAb NM-01, which binds the V3 loop sequence GPGR and neutralizes the MN and IIIB strains of HIV-1 (Ohno, T., et al., Proc. Natl. Acad. Sci. USA 88:10726–10729, 1991), strongly neutralized each of the five chimeric viruses (with titers of 2.1 to 9.1 ng/ml) irrespective of their sequences. HuMAb 694/98-D, which binds the V3 loop sequence GRAF and neutralizes the MN, IIIB, ALA-1, SF2, and WMJ2 strains (Gorny, M. K., et al., J. Virol. 66:7538–7542, 1992), neutralized the chimeras to different degrees (with titers ranging from 4.7 to 250 ng/ml). MuMAb 59.1, which binds GPGRAF (White-Scharf, M. E., et al., Virology 192:197–206, 1993 and Ghiara, J. B., et al., Science 264:82–85, 1994) and neutralizes the MN and IIIB strains (White-Scharf, M. E., et al., Virology 192:197–206, 1993), potently neutralized all of the chimeras (with titers of 2.1–4.7 ng/ml), except for D6-4 (which it neutralized with a titer of 53.8 ng/ml). There was nearly a 20-fold range of titers (1:21,500–1:408,700) for the chimeric viruses neutralized by the guinea pig PAb anti-MN octamer p200M, which neutralizes the MN and IIIB strains (Wang, C. Y., et al., Science 254:285–288, 1991), whereas the titers observed for neutralization by guinea pig PAb anti-IIIB octamer pl27, which neutralizes the IIIB, MN, and RF strains (Wang, C. Y., et al., Science 254:285–288, 1991), were quite similar to each other (1:34,000–1:89,700). In contrast, none of the chimeric viruses were neutralized by MuMAb 50.1, capable of neutralizing the MN and IIIB strains (White-Scharf, M. E., et al., Virology 192:197–206, 1993), at the concentrations tested (~500 ng/ml). The epitope of this antibody has been mapped serologically to RIHIG (White-Scharf, M. E., et al., Virology 192:197–206, 1993) and structurally to KRIHIGP (Rini, J. M., et al., Proc. Natl. Acad. Sci. USA 90:6325–6329, 1993) of which only the H, I, G, and P are present in any of the chimeras. Likewise, at the concentrations tested (~500 ng/ml), none of the chimeric viruses were neutralized by the IIIB type-specific MuMAb 0.5β which binds the V3 loop between gp120 residues 308 and 331 (Matsushita, S., et al., J. Virol. 62:2107–2114, 1988 and Masuda, T., et al., J. Immunol. 145:3240–3246, 1990). Wild-type HRV14 was not neutralized by any of the monoclonal or polyclonal antibody preparations at the concentrations tested (<500 ng/ml and >1:382, respectively).

F. IMMUNIZATION OF GUINEA PIGS 30 to 90 μg of purified chimeric virus were inoculated subcutaneously into each of three guinea pigs (Dunkin Hartley, Cocalico Biologicals, Reamstown, Pa.). The following inoculation schedules (given in weeks) were employed: D6-4: 0, 3, 6; DN-1: 0, 4, 8; DN-6: 0, 5, 9; DN-7: 0, 3, 6; and DN-9: 0, 5, 8. Sera were collected prior to immunization and at two weeks after the primary boost and 2 and 4 weeks after the final boost. 40 μg of purified HRV14 were inoculated subcutaneously into each of two guinea pigs (Dunkin Hartley, United Biomedical, Inc.) on weeks 0, 5, and 10. Sera were collected on weeks 11.5 and 13. Freund's Complete Adjuvant was used for all primary immunizations; Freund's Incomplete Adjuvant was used for all boosts.

G. ELISAS AGAINST PEPTIDES CONTAINING SEQUENCES OF THE V3 LOOP

The peptides used in the enzyme-linked immunosorbent assays (ELISAs) are shown in Table 5. Conditions for the ELISAs were modified from Wang et al. (Wang, J. J. G., et al., Proc. Natl. Acad. Sci. USA 83:6159–6163, 1986). Antisera against each of the five chimeric viruses were capable of reacting well with multiple peptides. FIG. 1 shows ELISA titers corresponding to the reactivity of anti-chimera antisera (at dilutions of 1:8000 for three guinea pigs per chimera; DN-9 titers not shown) with V3 loop peptides derived from seven strains of HIV-1 (Table 5). In general, the antisera recognized peptides with sequences from the MN, SC, and WMJ2 strains best, the IIIB and SF2 isolates less well, and the Uganda and Thai isolates the least well. None of the antisera showed reactivity to peptides with sequences from the Brazil or RF isolates (at dilutions of 1:1000). Antisera directed against wild-type HRV14 as well as each of the preimmunization antisera did not react with any of the peptides (at dilutions of 1:1000).

H. HIV-1 NEUTRALIZATION ASSAYS

Neutralization assays were based on the Std. SN assay described by White-Scharf et al. (White-Scharf, M. E., et al., Virology 192:197–206, 1993). Reverse transcriptase (RT) activity was determined on day four according to Willey et al. (Willey, R. L., et al., J. Virol. 62:139–147, 1988). Antisera raised against each of the chimeras were tested for their ability to neutralize HIV-1 ALA-1, MN, and IIIB in cell culture (Table 7).

TABLE 7

NEUTRALIZATION OF HIV-1 BY CHIMERA ANTISERA

| Virus | ALA-1 | | MN | | IIIB | |
|---|---|---|---|---|---|---|
| antisera | 90% | 60% | 90% | 60% | 90% | 60% |
| D6-4 | — | 19 | — | — | — | — |
| DN-1 | 40 | 80 | — | — | — | — |
| | — | 22 | — | — | — | — |
| DN-6 | 550 | 2600 | 40 | 1125 | — | — |
| | 9 | 38 | — | — | — | — |
| DN-7 | 17 | 77 | — | — | 5 | 22 |
| DN-9 | — | 5 | — | 7 | — | — |
| HRV14 | — | — | — | — | — | — |

Titers are expressed as the reciprocals of the dilutions that inhibited reverse transcription by 90% or 60% relative to values obtained using normal guinea pig serum. A dash indicates lack of neutralization at reciprocal dilutions > or = 4. Each line of data corresponds to titers for one guinea pig. Three guinea pigs were immunized with each chimeric virus; two guinea pigs were immunized with HRV14.

Chimeric virus DN-6 elicited the most potent antiserum obtained, with one of three antisera able to neutralize the ALA-1 and MN strains of HIV-1 at 90% inhibition titers of 550 and 40, respectively, and 60% inhibition titers of 2600 and 1125, respectively. DN-1 was able to elicit a neutralizing response against ALA-1 in one guinea pig with a 90% inhibition titer of 40 and a 60% inhibition titer of 80 as well as a neutralizing response against ALA-1 in another guinea pig with a 60% inhibition titer of 22. One antiserum directed against DN-7 neutralized ALA-1 with a 90% inhibition titer of 17 and a 60% inhibition titer of 77 and cross-neutralized IIIB with a 90% inhibition titer of 5 and a 60% inhibition titer of 22. D6-4 elicited a neutralizing response against ALA-1 in one guinea pig with a 60% inhibition titer of 19. DN-9 elicited only marginal neutralizing responses. Antisera raised against wild-type HRV14 were unable to neutralize any of the HIV-1 isolates with a 90% or 60% inhibition titer of 24.

As shown in Table 8, the 90% HIV-1 inhibition titer of 550 that was obtained for chimeric virus DN-6 is comparable to the titers obtained for several HIV immunogens that have recently been announced to be the subjects of clinical trials in humans. While direct comparisons are complicated by differences among the assays and species of vaccines, the ability of the method of the present invention to find such a strong immunogen within such a small set of immunoselected chimeras suggests that this approach has the potential to yield vaccine candidates of even greater potency.

TABLE 8

| IMMUNOGEN[a] | SOURCE STRAIN | ANIMAL IMMUNIZED | HIV TEST STRAIN | RECIPROCAL NEUT'N TITER | ASSAY[b] | CLINICAL TRIALS | REF. |
|---|---|---|---|---|---|---|---|
| | | | CHIMERIC VIRUSES | | | | |
| HRV: V3 loop mimotope | None | guinea pigs | ALA-1 | 550 | 3 | | 1 |
| Polio: gp41 (aa 735–752) | IIIB | rabbits | RF, SF2, IIIB, SF33, Z84, & CB24 | 10–80 | 1 | | 2 |
| Polio: V3 loop | LAI | rabbits | LAI | 100 | 1 | | 3 |
| Influenza: V3 loop | MN | mice | MN | 320–640 | 4 | | 4 |
| Influenza: gp41 (aa 662–668) | Many (uses a conserved sequence) | mice | MN, RF & IIIB | 58–320 | $1^c$ | | 5 |
| | | | RF & MN | ~100–180 | 4 | | |
| | | | VIRUS-LIKE PARTICLES | | | | |
| p24, gp120 & gp41 | BRU | rabbits | BRU | 24–64 | 4 | | 6 |
| TY: V3 loop | HXB2 | rabbits | IIIB | 64–2,048 | 1 | | 7 |
| HBsAg: V3 loop | BRU | macaques | BRU | 252 | 1,3 | | 8 |
| | | | ENVELOPE PROTEINS | | | | |
| Vaccinia virus (vv) gp160 (V25) | IIIB | humans | IIIB & RF | >100 | $1^c$, $2^c$ | Yes | 9 |
| gp120 (non-glycosylated, denatured) | SF2 | guinea pigs | SF2 & BRU | ~20 | 4 | | 10 |
| gp120 (non-glycosylated, denatured) | SF2 | humans | SF2 | 55–232 | $?^c$ | Yes | 11 |
| | | | MN | 2–9 | $?^c$ | | |
| sgp160 | IIIB | baboons | IIIB | 5–20 | $4^c$ | | 12 |
| sgp160 | IIIB | rabbits | IIIB | 14–46 | $3^c$ | | 13 |
| gp120 | IIIB | rabbits | IIIB | 160–256 | $3^c$ | | 13 |
| sgp160 | IIIB | chimps | IIIB | 160 | 2 | | 14 |
| gp120 | IIIB | chimps | IIIB | 320–640 | 2 | | 14 |
| gp120 | MN | rabbits | MN, CC, IIIB, Du6587-5, Du4489-5, & Du6587-7 | 22–780 | 3 | | 15 |
| gp120 | IIIB | humans | IIIB | <10–40 | 1 | Yes | 16 |
| | | | IIIB | <10–168 | 3 | | |
| | | | MN | <10–105 | 3 | | |
| gp120 | MN | baboons | MN | ~15–80 | $2^c$ | | 17 |
| gp160 | IIIB | goats | IIIB | <5–80 | 3 | | 18 |
| | | | RF | <5–20 | 3 | | |
| gp160 | IIIB | humans | IIIB | 320 | 3 | | 18 |
| | | | RF | 80–160 | 3 | | |
| gp160 | IIIB | humans | IIIB | 10 | $1^c$ | Yes | 19 |
| | | | | 38 | $3^c$ | | |
| gp160 | IIIB | humans | IIIB | 13–25 | 2 | Yes | 20 |
| gp160 | IIIB | humans | IIIB | <16–128 | 2 | Yes | 21 |
| gp160 | IIIB | humans | LAV | <4–9 | 4 | Yes | 22 |
| gp160 V3 pep.-KLH ± p18 or inactiv'd HIV BRU | IIIB (±BRU) | chimps | IIIB | 64–1024 | 1 | | 23– |
| | | | | 50–800 | 2 | | 25 |
| gp160 ± (p18 + V3 + T1 peps.) ± vvgp160 (V25) | IIIB | humans | IIIB, MN, RF, & Ch88 | 60–320 | $2^c$ | Yes | 26 |
| vvgp160 (HIVAC-le) + gp160 | IIIB | humans | IIIB | <10–40 | $1^c$ | Yes | 27 |
| vvgp160 (HIVAC-le) + gp160 | IIIB | humans | IIIB | 5–80 | $1^c$ | Yes | 28 |
| | | | | 10–90 | 3 | | |
| Adenovirus: gp160 | IIIB | dogs | IIIB | 30–930 | $2^d$ | Yes | 29 |
| | MN | dogs | MN | ≧20 | $2^d$ | Yes | 29 |
| Adenovirus: gp160 | IIIB | chimps | IIIB | 10–40 | $2^d$ | | 30 |
| DNA-gp160 | IIIB | mice | IIIB | 22–160 | 2 | | 31 |
| | | | | 100 | 1 | | |

TABLE 8-continued

| IMMUNOGEN[a] | SOURCE STRAIN | ANIMAL IMMUNIZED | HIV TEST STRAIN | RECIPROCAL NEUT'N TITER | ASSAY[b] | CLINICAL TRIALS | REF. |
|---|---|---|---|---|---|---|---|
| PEPTIDES | | | | | | | |
| Octameric peptides-heptalysyl cores | IIIB | guinea pigs | IIIB | 256->19,683 | 4 | | 32 |
| | | | RF | 65 | 4 | | |
| | | | MN | 512 | 4 | | |
| | MN | | IIIB | 128 | 4 | | |
| | | | MN | 8,912 | 4 | | |
| | Hexavalent (MN, RF, IIIB, SC, SF2, & WMJ2) | | IIIB | 1,024 | 4 | | |
| | | | MN | 4,096 | 4 | | |
| Octameric peptides-heptalysyl cores | MN | humans | ND[e] | ~32 | 5 | Yes | 33 |
| V3 peptides in liposomes | IIIB | mice & guinea pigs | IIIB | 8 | 3 | | 34 |
| p17 peptide-HGP30 | SF2 | humans | ND[e] | ND[e] | ND[e] | Yes | 35 |
| $T_H$ + p18 peptides | IIIB | mice | IIIB | 816,384 | 1 | | 36 |
| | | | MB | 64 ≥ 512 | 1[c] | | |
| Randomized peptides-OMPC | None | rabbits | SF2 | 80–160 | 2 | | 37 |
| | | | ALA-1 | 20 | 2 | | |
| Cylic peptides - OMPC | IIIB | rabbits | IIIB, ALA-1, SF2, WMJ2, & Du6587-5 | 10–160 | 2 | | 38 |
| | MN | rabbits | MN, ALA-1, SF2, WMJ2, Du6587-5, & IIIB | 20–640 | 2 | | 38 |

[a]Brackets indicate related studies using the same immunogen(s)
[b]Neutralization assays
1 Inhibition of syncytium forming units (90–100% inhibition)
2 Cytopathic effect (90–100% inhibition)
3 Reverse transcriptase activity (90% inhibition)
4 p24 production (>70% inhibition)
5 Inhibition of multiple virus dose (% inhibition unknown)
[c]50% inhibition
[d]40% Inhibition
[e]No data

TABLE 8 REFERENCES

1. Resnick, D A, et al., Chimeras from a human rhinovirus 14:human immunodeficiency virus type 1 V3 loop seroprevalance library induce neutralizing responses against HIV-1, J. Virology, in press (1995).
2. Evans, D J, et al., An engineered poliovirus chimera elicits broadly reactive HIV-1 neutralizing antibodies, Nature, 339, 385–388 (1989).
3. Dedieu, J-F, et al., Poliovirus chimeras expressing sequences from the principal neutralization domain of human immunodeficiency virus type 1, J. Virol., 66, 3161–3167 (1992).
4. Li, S, et al., Chimeric influenza virus induces neutralizing antibodies and cytotoxic T cells against human immunodeficiency virus type 1, J Virol., 67, 6659–6666 (1993).
5. Muster, T, et al., Cross-neutralizing activity against divergent human immunodeficiency virus type 1 isolates induced by the gp41 sequence ELDKWAS, J. Virol., 68, 4031–4034 (1994).
6. Haffar, O K, et al., HIV-specific humoral and cellular immunity in rabbits vaccinated with recombinant human immunodeficiency virus-like gag-env particles., Virology, 183, 487–495 (1991).
7. Griffiths, J, C., et al., Induction of high-titer neutralizing antibodies using hybrid human immunodeficiency virus V3-Ty viruslike particles in a clinically relevant adjuvant., J. Virol., 65, 450–456 (1991).
8. Schlienger, K, et al., Human immunodeficiency virus type 1 major neutralizing determinant exposed on hepatitis B surface antigen particles is highly immunogenic in primates, J. Virol., 66, 2570–2576 (1992).
9. Zagury, D, et al., A group specific anamnestic immune reaction against HIV-1 induced by a candidate vaccine against AIDS, Nature, 332, 728–731 (1988).
10. Steimer K S, et al., Recombinant env and gag polypeptides in characterizing HIV-1-neutralizing antibodies, Vaccines 88, 347–355 (1988).
11. Kahn, J O, et al., Clinical and immunologic responses to human immunodeficiency virus (HIV) type 1 SF2 gp120 subunit vaccine combined with MF59 adjuvant with or without muramyl tripeptide dipalmitoyl phosphatidylethanolamine in non-HIV-infected human volunteers, J. Infect. Dis., 170, 1288–1291 (1994).
12. Anderson, K P, et al., Effect of dose and immunization schedule on immune response of baboons to recombinant glycoprotein 120 of HIV-1, J. Infect. Dis., 160, 960–969 (1989).
13. Berman, P W, et al., Expression and immunogenicity of the extracellular domain of the human immunodeficiency virus type 1 envelope glycoprotein, gp160, J. Virol., 63, 3489–3498 (1989).
14. Berman, P W, et al., Protection of chimpanzees from infection by HIV-1 after vaccination with recombinant glycoprotein gp120 but not gp160, Nature, 345, 622–625 (1990).

15. Berman, P W, et al., Neutralization of multiple clinical isolates of HIV-1 by antisera raised against a monovalent subunit vaccine, Sixieme Colloque des Cent Gardes, 293–297 (1991).
16. Schwartz, D H, et al., Induction of HIV-1-neutralising and syncytiuminhibiting antibodies in uninfected recipients of HIV-1IIIB rgp120 subunit vaccine, Lancet, 342, 69–73 (1993).
17. Powell, M F, et al., Immunogenicity and HIV-1 virus neutralization of MN recombinant glycoprotein 120/HIV-1 QS21 vaccine in babbons, AIDS Res. Hum. Retroviruses, 10, S105–S108 (1994).
18. Barrett, N, et al., Large-scale production and purificaiton of a vaccinia recombinant-derived HIV-1 gp160 and analysis of its immunogenicity, AIDS Res. Hum. Retroviruses, 5, 159–171 (1989).
19. Belshe, R B, et al., Safety and immunogenicity of a fully glycosylated recombinant gp160 human immunodeficiency virus type 1 vaccine in subjects at low risk of infection, J. Infect. Dis., 168, 1387–1395 (1993).
20. Gorse, G J, et al., HIV-1 recombinant gp160 vaccine given in accelerated dose schedules, Clin. Exp. Immunol., 98, 178–184 (1994).
21. Dolin, R, et al., The safety and immunogenicity of a human immunodeficiency virus type 1 (HIV-1) recombinant gp160 candidate vaccine in humans, Ann. Intern. Med., 114, 119–127 (1991).
22. Kovacs, J A, et al., Induction of humoral and cell-mediated anti-human immunodeficiency virus (HIV) responses in HIV sero-negative volunteers by immunization with recombinant gp160, J. Clin. Invest., 92, 919–928 (1993).
23. Girard, M, et al., Immunization of chimpanzees confers protection against challenge with human immunodeficiency virus, Proc. Natl. Acad. Sci. USA, 88, 542–546 (1991).
24. Belo, M, et al., Antibody-dependent cellular cytotoxicity against HIV-1 in sera of immunized chimpanzees, AIDS, 5, 169–176 (1991).
25. Fultz, P N, et al., Vaccine protection of chimpanzees against challenge with HIV-1-infected peripheral blood mononuclear cells., Science, 256, 1687–1690 (1992).
26. Picard, O, et al., A 2-year follow-up of an anti-HIV immune reaction in HIV-1 gp160-immunized healthy seronegative humans: evidence for persistent cell-mediated immunity, J. Acquir. Immune Defic. Syndr., 5, 539–546 (1992).
27. Cooney, E L, et al., Enhanced immunity to human immunodeficiency virus (HIV) envelope elicited by a combined vaccine regimen consisting of priming with a vaccinia recombinant expressing HIV envelope and boosting with gp160 protein, Proc. Natl. Acad. Sci. USA, 90, 1882–1886 (1993).
28. Graham, B S, et al., Augmentation of human immunodeficiency virus type 1 neutralizing antibody by priming with gp160 recombinant vaccinia and boosting with rgp160 in vaccinia-naive adults, J. Infect. Dis., 167, 533–537 (1993).
29. Natuk, R J, et al., Adenovirus-human immunodeficiency virus (HIV) envelope recombinant vaccines elicit high-titered HIV-neutralizing antibodies in the dog model, Proc. Natl. Acad. Sci. USA, 89, 7777–7781 (1992).
30. Natuk, R J, et al., Immunogenicity of recombinant human adenovirus-human immunodeficiency virus vaccines in chimpanzees, AIDS Res. Hum. Retroviruses, 9, 395–404 (1993).
31. Wang C Y, et al., Long-term high-titer neutralizing activity induced by octameric synthetic HIV-1 antigen, Science, 254, 285–288 (1991).
32. Wang B, et al., Gene inoculation generates immune responses against human immunodeficiency virus type 1, Proc. Natl. Acad. Sci. USA, 90, 4156–4160 (1993).
33. Gorse, G J, et al., Evaluation of HIV-1 MN V3 octameric peptide vaccine, Seventh Annual Meeting of the National Cooperative Vaccine Development Groups for AIDS, 94 (1994).
34. Defoort, J-P, Nardelli, B, Huang, W, Ho, D D, and Tam, J P, Macromolecular assemblage in the design of a synthetic AIDS vaccine, Proc. Natl. Acad. Sci. USA, 89, 3879–3883 (1992).
35. Kahn, J O, et al., A phase I study of HGP-30, a 30 amino acid subunit of the human immunodeficiency virus (HIV) p17 synthetic peptide analogue subunit vaccine in seronegaive subjects, AIDS Res. Hum. Retroviruses, 8, 1321–1322 (1992).
36. Ahlers, J D, et al., Construction of an HIV-1 peptide vaccine containing a multideterminant helper peptide linked to a V3 loop peptide 18 inducing strong neutralizing antibody responses in mice of multiple MHC haplotypes after two immunizations, J. Immunol., 150, 5647–5665 (1993).
37. Keller, P M, et al., Identification of HIV vaccine candidate peptides by screening random phage epitope libraries, Virology, 193, 709–716 (1993).
38. Tolman, R L, et al., Cyclic V3-loop-related HIV-1 conjugate vaccines, Int. J. Pept. Pro. Res., 41, 455–466 (1993).

I. CRYSTALLIZATION OF CHIMERAS

Crystals of DN-6 were obtained based on the crystallization conditions of Arnold et al. (Arnold, E., et al., J. Mol. Biol. 177:417–430, 1984) that diffracted X-rays beyond 2.8 Å resolution. Purified samples of D6-4, DN-6, and DN-1 (P3 stocks) were suspended in 10 mM Tris-HCl, pH 7.2, 100–200 mM NaCl at a concentration of 15 mg virus/ml. One set of vapor diffusion hanging drops (modified from Arnold, E., et al., J. Mol. Biol. 177:417–430, 1984) initially contained 7.5 mg virus/ml, 10 mM Tris-HCl, pH 7.2, 50–100 mM NaCl, 10 mM $CaCl_2$, and 0.25–0.38% PEG 8000. The corresponding reservoirs contained 10 mM Tris-HCl, pH 7.2, 100 mM NaCl, 20 mM $CaCl_2$, and 0.5–0.75% PEG 8000. In another set (modified from Erickson, J. W., et al., Proc. Natl. Acad. Sci. USA 80:931–934, 1983), the drops initially contained 5–7.5 mg virus/ml, 50 mM $NaHPO_4$, pH 7.2, 50 mM NaCl, and 8–10% saturated ammonium sulfate and the reservoirs contained a two-fold-concentrated version of the corresponding hanging drop solution (excluding virus).

Crystals were irradiated by X-rays of 0.91 Å wavelength using the F1 beamline at the Cornell High Energy Synchrotron Source. Diffraction patterns were collected using Fuji image plates and the data were processed using DENZO (Otwinowski, Z. (1993) Yale University, New Haven).

As many as 9 useful 0.3° oscillation images were obtained from one crystal. A preliminary analysis shows that the unit cell is orthorhombic and the cell dimensions are a=318.1 Å, b=355.6 Å, and c=378.7 Å. Crystals of D6-4 were obtained that diffracted X-rays to comparable resolution.

The plasmid pWR40 containing a complete cDNA sequence of HRV14 has been deposited for 30 years at the American Type Culture Collection (ATCC) in Rockville, Md. and assigned Accession No. ATCC VR Y.

The present invention is not to be limited in scope by the virus-encoding plasmid deposited, since the deposited embodiment is intended to serve as a single illustration of one aspect of the invention and any plasmids or viruses which are functionally equivalent are within the scope of this invention. The deposit of material does not constitute an admission that the written description contained herein is inadequate to enable the practice of any aspect of the invention, including the best mode, or is the deposit to be construed as limiting the scope of the claims to the specific illustrations that they represent. In point of fact, it will become apparent to those of skill in the art that various modifications of the invention, in addition to those shown and described herein, are readily possible. It is intended that such modifications fall within the scope of the appended claims. Unless indicated otherwise, all references cited herein are hereby incorporated by reference in their entirety.

We claim:

1. Biologically pure recombinant chimeric human rhinovirus constructed by inserting into the nucleotide sequence of a human rhinovirus encoding part of a neutralizing immunogenic site, a heterologous nucleotide sequence encoding a chimeric region, wherein the chimeric region is expressed on the surface of the chimeric rhinovirus and is capable of participating in an immune reaction.

2. The chimeric rhinovirus of claim 1, wherein the rhinovirus binds to intercellular adhesion molecule 1 (ICAM-1).

3. The chimeric rhinovirus of claim 1, wherein the chimeric region is presented in the portion of viral protein VP2 of NIm-II.

4. The chimeric rhinovirus of claim 1, wherein the chimeric region is presented in the portion of viral protein VP1 of NIm-IA.

5. The chimeric rhinovirus of claim 1, wherein the chimeric region is of viral origin.

6. The chimeric rhinovirus of claim 5, wherein the chimeric region is derived from a neutralizing immunogenic site or a receptor site.

7. The chimeric rhinovirus of claim 5, wherein the viral origin of the chimeric region is an orthomyxovirus.

8. The chimeric rhinovirus of claim 7, wherein the orthomyxovirus is influenza virus.

9. The chimeric rhinovirus of claim 8, wherein the chimeric region is from the hemagglutinin antigen of the influenza virus.

10. The chimeric rhinovirus of claim 9, wherein the chimeric region is from about amino acid 128 to about amino acid 136 of the hemagglutinin antigen.

11. The chimeric rhinovirus of claim 5, wherein the viral origin of the chimeric region is a picornavirus.

12. The chimeric rhinovirus of claim 11, wherein the picornavirus is poliovirus.

13. The chimeric rhinovirus of claim 12, wherein the chimeric region is from the N-Ag1 site of the poliovirus.

14. The chimeric rhinovirus of claim 13, wherein the chimeric region is from about amino acid 93 to about amino acid 100 of the N-Ag1 site.

15. The chimeric rhinovirus of claim 12, wherein the polio virus is type 3.

16. The chimeric rhinovirus of claim 5, wherein the viral origin of the chimeric region is a retrovirus.

17. The chimeric rhinovirus of claim 16, wherein the retrovirus is a human immunodeficiency virus.

18. The chimeric rhinovirus of claim 17, wherein the human immunodeficiency virus is selected from the group consisting of HIV-1 and HIV-2.

19. The chimeric rhinovirus of claim 17, wherein the chimeric region of the human immunodeficiency virus is selected from the group consisting of the gag and env proteins.

20. The chimeric rhinovirus of claim 17, wherein at least a portion of the chimeric region as translated comprises at least a portion of the V3 loop of the gp120 envelope glycoprotein of HIV-1.

21. The chimeric rhinovirus of claim 20, wherein the chimeric region is presented at loop 2 of viral protein VP2 of NIm-II immunogenic site of HRV14.

22. The chimeric rhinovirus of claim 21, wherein the chimeric region is presented between from about amino acid 159 to about amino acid 161 of VP2.

23. The chimeric rhinovirus of claim 20, wherein at least a portion of the chimeric region as translated comprises N-Ile Gly Pro Gly Arg Ala Phe (SEQ ID NO:23).

24. The chimeric rhinovirus of claim 1, wherein the chimeric region of the rhinovirus is of non-viral origin.

25. The chimeric rhinovirus of claim 24, wherein the chimeric region is derived from a source selected from the group consisting of a neoplasm, a parasite, and a bacterium.

26. The chimeric rhinovirus of claim 1, wherein multiple neutralizing sites of the chimeric rhinovirus contain a chimeric region.

27. The chimeric rhinovirus of claim 26, wherein the chimeric region at each neutralizing site is different.

* * * * *

UNITED STATES PATENT AND TRADEMARK OFFICE
CERTIFICATE OF CORRECTION

PATENT NO. : 5,714,374

DATED : 3 February 1998

INVENTOR(S) : Edward V. ARNOLD et al.

Page 1 of 4

It is certified that error appears in the above-identified patent and that said Letters Patent is hereby corrected as shown below:

| Column | Line | |
|---|---|---|
| 1 | 11 | Change "rems" to --terms--. |
| 14 | 49 | Change "infectionby" to --infection by--. |
| 17 | 4 | Change "HRV14:HAN Im-II" to --HRV14:HA $N_{Im}$-II--. |
| 17 | 19 | Change "10 mMTris-HCl" to -- 10mM Tris-HCI |
| 18 | 11 | Change "In vitro" to --*In vitro*--. |

UNITED STATES PATENT AND TRADEMARK OFFICE
CERTIFICATE OF CORRECTION

PATENT NO. : 5,714,374  Page 2 of 4

DATED : 3 February 1998

INVENTOR(S) : Edward V. ARNOLD et al.

It is certified that error appears in the above-identified patent and that said Letters Patent is hereby corrected as shown below:

Column   Line

22           Table 4    Delete Table 4 and insert the following corrected Table 4:

TABLE 4

Amino acid sequences of Nlm-II inserts[6]

| Linker | Varied HIV-1 sequences | HIV-1 core | Varied HIV-1 sequences | | | | Linker |
|---|---|---|---|---|---|---|---|
| | 93% | 53% | 95% | 94% | 97% | 89% | |
| XX | H(50/45) | IGPGRAF | Y(80/72) | T(55/60) | T(88/81) | G(75/81) | XX |
| X  | T(10/5)  |         | V(6/1)   | A(39/40) | A(4/9)   | E(6/9)   | XX |
| —  | P(10/15) |         | H(5/9)   |          | I(4/5)   | R(4/9)   | XX |
| XX | R(10/15) |         | F(2/8)   |          | R(1/4)   | K(4/1)   | X  |
| X  | N(7/15)  |         | L(2/1)   |          | G(0/0.5) |          | X  |
| —  | S(6/5)   |         | D(0.3/9) |          | V(0/0.5) |          | X  |
| XX |          |         |          |          |          |          | —  |
| X  |          |         |          |          |          |          | —  |
| —  |          |         |          |          |          |          | —  |

[6]The approximate percentages of sequenced HIV-1 isolates containing any of the residues encoded are shown. In Parentheses, the first number corresponds to the percentage among the 354 known sequences; the second number corresponds to the percentage encoded in the HRV14:HIV-1 library.

UNITED STATES PATENT AND TRADEMARK OFFICE
CERTIFICATE OF CORRECTION

PATENT NO. : 5,714,374
DATED : 3 February 1998
INVENTOR(S) : Edward V. ARNOLD et al.

It is certified that error appears in the above-identified patent and that said Letters Patent is hereby corrected as shown below:

| Column | Line | |
|---|---|---|
| 22 | 67 | Change "(MuMLAb)" to --(MuMab)--. |
| 23 | 37 | Change "vital" to --viral--. |
| 23 | Table 5 | Change "DATER" to --DATER--; change "HATES" to --HATES--; change "YATEH" to --YATEH--; Change "HATGE' to --HATGE--. |
| 25 | Table 6 | Change "DN-7" to --DN-6--; change "DN-6" to --DN-7--. |

UNITED STATES PATENT AND TRADEMARK OFFICE
CERTIFICATE OF CORRECTION

PATENT NO. : 5,714,374

DATED : 3 February 1998

INVENTOR(S) : Edward V. ARNOLD et al.

It is certified that error appears in the above-identified patent and that said Letters Patent is hereby corrected as shown below:

| Column | Line |
|---|---|
| 28 | Table 8, column "RECIPROCAL NEUT'N TITER" change "-20" to --~20--. |
| | Table 8, column "RECIPROCAL NEUT'N TITER" change "<4---9" --<4- ~9--. |

Signed and Sealed this

Eleventh Day of May, 1999

Attest:

Q. TODD DICKINSON

Attesting Officer     Acting Commissioner of Patents and Trademarks

SEQUENCE LISTING ( 1 ) GENERAL INFORMATION:

( i i i ) NUMBER OF SEQUENCES: 23

( 2 ) INFORMATION FOR SEQ ID NO: 1 :

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 1 :

Ser Ser Ala Asn Glu Val Gly Gly Pro
              5

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 2 :

Thr Gly Val Thr Gln Asn Gly Gly Ser
              5

( 2 ) INFORMATION FOR SEQ ID NO: 3 :

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 3 :

Ser Gly Val Thr Gln Asn Gly Gly Pro
              5

( 2 ) INFORMATION FOR SEQ ID NO: 4 :

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 4 :

Ile Gln Asn Lys Asp Ala Thr Gly Ile Asp Asn His Arg Glu Ala Lys
            5                        10                        15

Leu Phe ( 2 ) INFORMATION FOR SEQ ID NO: 5 :

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION:SEQ ID NO: 5 :

Val Asp Asn Glu Gln Pro Thr Thr Arg Ala Asp Lys Leu Phe
            5                      10

( 2 ) INFORMATION FOR SEQ ID NO: 6 :

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION:SEQ ID NO: 6 :

Val Asp Asn Asp Ala Pro Thr Lys Arg Ala Ser Lys Leu Phe
            5                      10

( 2 ) INFORMATION FOR SEQ ID NO: 7 :

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION:SEQ ID NO: 7 :

Ile Gln Asn Glu Gln Pro Thr Thr Arg Ala Gln Lys Leu Phe
            5                      10

( 2 ) INFORMATION FOR SEQ ID NO: 8 :

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION:SEQ ID NO: 8:

Ile Gln Asn Asp Ala Pro Thr Lys Arg Ala Ser Lys Leu Phe
            5                      10

( 2 ) INFORMATION FOR SEQ ID NO: 9 :

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: peptide ( x i ) SEQUENCE DESCRIPTION:SEQ ID NO: 9 :

Glu Ser Val Gln Ile Asn Cys Thr Arg Pro Asn Tyr Asn Lys Arg Lys
            5                      5                        15

Arg Ile His Ile Gly Pro Gly Arg Ala Phe Tyr Thr Thr Lys Asn Met
          20                25                      30

( 2 ) INFORMATION FOR SEQ ID NO: 10 :

( i ) SEQUENCE CHARACTERISTICS:
    ( A ) LENGTH: 27 amino acids ( B ) TYPE: amino acid
( D ) TOPOLOGY: linear ( i i ) MOLECULE TYPE: peptide ( x i ) SEQUENCE DESCRIPTION:SEQ ID NO: 10 :

Gln Ser Val Glu Ile Asn Cys Thr Arg Pro Asn Asn Asn Thr Arg Lys
                 5                      10                      15
Ser Ile Arg Gln Arg Val Thr Ile Gly Lys Ile
             20                  25

( 2 ) INFORMATION FOR SEQ ID NO: 11 :

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 11 :

Lys Ser Ile Tyr His Thr Thr Gly
                 5

( 2 ) INFORMATION FOR SEQ ID NO: 12 :

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 12 :

Glu Ala Val Glu Ile Asn Cys Thr Arg Pro Asn Asn Asn Thr Thr Lys
                 5                      10                      15
Ser Ile His Tyr Ala Thr Gly Asp Met
             20                  25

( 2 ) INFORMATION FOR SEQ ID NO: 13 :

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 13 :

Glu Ser Val Glu Ile Asn Cys Thr Arg Pro Tyr Asn Asn Val Arg Arg
                 5                      10                      15
Ser Leu Ser Arg Thr Arg Glu Met
             20

( 2 ) INFORMATION FOR SEQ ID NO: 14 :

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 14 :

Glu Ser Val Thr Ile Asn Cys Thr Arg Pro Tyr Ser Asn Thr Arg Gln
                 5                      10                      15
Gly Thr His Tyr Cys Thr Ser Gly Tyr Met (2) INFORMATION FOR SEQ ID NO: 15:

(i) SEQUENCE CHARACTERISTICS:
(A) LENGTH: 28 amino acids
(B) TYPE: amino acid
(D) TOPOLOGY: linear (ii) MOLECULE TYPE: peptide (xi) SEQUENCE DESCRIPTION:SEQ ID NO: 15:

Glu Ser Val Glu Ile Asn Cys Thr Arg Pro Asn Asn Asn Thr Arg Lys
                  5                  10                      15
Ser Ile His Leu Gln Trp Tyr Thr Thr Gly Gln Met
              20              25

(2) INFORMATION FOR SEQ ID NO: 16:

(i) SEQUENCE CHARACTERISTICS:
(A) LENGTH: 29 amino acids
(B) TYPE: amino acid
(D) TOPOLOGY: linear (ii) MOLECULE TYPE: peptide (xi) SEQUENCE DESCRIPTION:SEQ ID NO: 16:

Glu Ser Val Val Ile Asn Cys Thr Arg His Asn Asn Thr Arg Lys
                  5                  10                  15
Ser Ile His Val Trp Ser Leu Phe Thr Thr Gly Glu Met
              20              25

(2) INFORMATION FOR SEQ ID NO: 17:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION:SEQ ID NO: 17:

Lys Ser Ile Thr Lys Val Ile Tyr Ala Thr Gly
                  5                  10

(2) INFORMATION FOR SEQ ID NO: 18:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION:SEQ ID NO: 18:

Pro Asp Ala Thr Glu Arg
                  5

(2) INFORMATION FOR SEQ ID NO: 19:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION:SEQ ID NO: 19:

His His Ala Thr Glu Ser
5

( 2 ) INFORMATION FOR SEQ ID NO: 20 :

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 20 :

Pro Tyr Ala Thr Glu His
5

( 2 ) INFORMATION FOR SEQ ID NO: 21 :

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 21 :

Pro His Ala Thr Gly Glu
5

( 2 ) INFORMATION FOR SEQ ID NO: 22 :

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 22 :

Pro His Val Thr Glu
5

( 2 ) INFORMATION FOR SEQ ID NO: 23 :

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION:SEQ ID NO: 23 :

Ile Glu Pro Glu Arg Ala Phe
5